(12) United States Patent
Marescaux et al.

(10) Patent No.: US 8,137,263 B2
(45) Date of Patent: Mar. 20, 2012

(54) ARTICULATING ENDOSCOPE INSTRUMENT

(75) Inventors: Jacques Francois Bernard Marescaux, Scharrachbergheim (FR); Jeffrey S. Melanson, Sturbridge, MA (US); Bernard Dallemagne, Beauafys (BE); Joel Leroy, Schiltigheim (FR); Didier Raoul Daniel Mutter, Vendenheim (FR); James P. Barry, Charlton, MA (US); Stefan Storz, Wurmlingen (DE); Martin Leonhard, Emmingen (DE)

(73) Assignee: Karl Storz Endovision, Inc., Charlton, MA (US)

( * ) Notice: Subject to any disclaimer, the term of this patent is extended or adjusted under 35 U.S.C. 154(b) by 1068 days.

(21) Appl. No.: 11/844,623

(22) Filed: Aug. 24, 2007

(65) Prior Publication Data

US 2009/0054733 A1    Feb. 26, 2009

(51) Int. Cl.
*A61B 1/00* (2006.01)
(52) U.S. Cl. ........ 600/101; 600/141; 600/146; 600/149; 606/1
(58) Field of Classification Search .......... 606/1, 45–46, 606/51–52, 205; 600/101, 104–108, 137, 600/141, 142, 146, 147, 149
See application file for complete search history.

(56) References Cited

U.S. PATENT DOCUMENTS

| | | | |
|---|---|---|---|
| 1,271,319 A * | 7/1918 | Hotsinpiller | 475/201 |
| 3,667,474 A | 6/1972 | Lapkin et al. | |
| 3,896,793 A | 7/1975 | Mitsui et al. | |
| 3,915,157 A | 10/1975 | Mitsui | |
| 3,924,608 A | 12/1975 | Mitsui | |
| 4,436,087 A | 3/1984 | Ouchi | |
| 4,483,562 A | 11/1984 | Schoolman | 294/19 |
| 4,653,476 A | 3/1987 | Bonnet | |
| 4,880,015 A | 11/1989 | Nierman | 128/751 |
| 4,949,706 A | 8/1990 | Thon | |
| 4,950,273 A * | 8/1990 | Briggs | 606/113 |
| 5,025,778 A | 6/1991 | Silverstein et al. | |
| 5,037,433 A | 8/1991 | Wilk et al. | |
| 5,254,130 A | 10/1993 | Poncet et al. | 606/206 |
| 5,259,366 A | 11/1993 | Reydel et al. | |
| 5,312,391 A | 5/1994 | Wilk | |
| 5,312,434 A * | 5/1994 | Crainich | 606/207 |
| 5,318,528 A | 6/1994 | Heaven et al. | 604/95 |
| 5,330,502 A * | 7/1994 | Hassler et al. | 606/205 |
| 5,344,428 A | 9/1994 | Griffiths | 606/205 |

(Continued)

FOREIGN PATENT DOCUMENTS

DE    19820486 A1    11/1998

(Continued)

OTHER PUBLICATIONS

Extended European Search Report; EP 08 01 4564; Oct. 28, 2008; 6 pages.

*Primary Examiner* — Ahmed Farah
(74) *Attorney, Agent, or Firm* — St. Onge Steward Johnston & Reens LLC

(57) ABSTRACT

An endoscopic surgical instrument is provided that includes a handle portion, an elongated middle portion, an articulating portion and a tool portion. The tool portion is steerable by control mechanisms disposed on the handle portion which are accessible to a single hand of a user of the endoscopic surgical instrument. The endoscopic surgical instrument is advantageously employed in a variety of endoscopic surgical techniques, including transgastric or transluminal surgery.

65 Claims, 11 Drawing Sheets

U.S. PATENT DOCUMENTS

| | | | |
|---|---|---|---|
| 5,353,784 A | 10/1994 | Nady-Mohamed | |
| 5,386,818 A | 2/1995 | Schneebaum et al. | |
| 5,454,827 A * | 10/1995 | Aust et al. | 606/170 |
| 5,474,057 A | 12/1995 | Makower et al. | |
| 5,483,951 A * | 1/1996 | Frassica et al. | 600/104 |
| 5,503,616 A | 4/1996 | Jones | |
| 5,569,164 A | 10/1996 | Lurz | |
| 5,582,609 A * | 12/1996 | Swanson et al. | 606/39 |
| 5,609,601 A * | 3/1997 | Kolesa et al. | 606/170 |
| 5,624,379 A | 4/1997 | Ganz et al. | 600/104 |
| 5,624,398 A | 4/1997 | Smith et al. | |
| 5,630,782 A | 5/1997 | Adair | |
| 5,674,181 A | 10/1997 | Iida | |
| 5,735,849 A * | 4/1998 | Baden et al. | 606/51 |
| 5,749,889 A | 5/1998 | Bacich et al. | |
| 5,766,196 A * | 6/1998 | Griffiths | 606/170 |
| 5,782,834 A * | 7/1998 | Lucey et al. | 606/22 |
| 5,820,546 A | 10/1998 | Ouchi | |
| 5,827,177 A | 10/1998 | Oneda et al. | |
| 5,833,656 A | 11/1998 | Smith et al. | |
| 5,885,207 A | 3/1999 | Iwasaka | |
| 5,904,647 A * | 5/1999 | Ouchi | 600/104 |
| 5,921,915 A * | 7/1999 | Aznoian et al. | 600/104 |
| 5,938,678 A * | 8/1999 | Zirps et al. | 606/170 |
| 5,954,692 A | 9/1999 | Smith et al. | |
| 5,993,461 A | 11/1999 | Abae | |
| 5,995,875 A | 11/1999 | Blewett et al. | |
| 6,059,719 A | 5/2000 | Yamamoto et al. | |
| 6,066,090 A | 5/2000 | Yoon | |
| 6,071,233 A | 6/2000 | Ishikawa et al. | |
| 6,106,521 A * | 8/2000 | Blewett et al. | 606/41 |
| 6,179,776 B1 | 1/2001 | Adams et al. | |
| 6,227,782 B1 * | 5/2001 | Bowling et al. | 411/114 |
| 6,296,635 B1 | 10/2001 | Smith et al. | |
| 6,352,503 B1 | 3/2002 | Matsui et al. | |
| 6,409,727 B1 | 6/2002 | Bales et al. | |
| 6,482,198 B1 * | 11/2002 | Overaker et al. | 606/1 |
| 7,029,435 B2 | 4/2006 | Nakao | |
| 7,060,024 B2 * | 6/2006 | Long et al. | 600/106 |
| 7,070,602 B2 | 7/2006 | Smith et al. | 606/143 |
| 2002/0128682 A1 * | 9/2002 | Prestel et al. | 606/205 |
| 2005/0113640 A1 | 5/2005 | Saadat et al. | |
| 2005/0234297 A1 * | 10/2005 | Devierre et al. | 600/153 |
| 2007/0167679 A1 | 7/2007 | Miyamoto et al. | |
| 2007/0167680 A1 | 7/2007 | Miyamoto et al. | |
| 2007/0260273 A1 | 11/2007 | Cropper et al. | |
| 2008/0269557 A1 | 10/2008 | Marescaux et al. | |
| 2008/0269562 A1 * | 10/2008 | Marescaux et al. | 600/142 |

FOREIGN PATENT DOCUMENTS

| | | |
|---|---|---|
| GB | 2325166 A | 11/1998 |
| JP | 10305037 A | 11/1998 |
| JP | 2002503131 T | 1/2002 |
| WO | 9856297 A1 | 12/1998 |
| WO | 0207611 A2 | 1/2002 |
| WO | 2005044095 A1 | 5/2005 |
| WO | 2006046263 A1 | 5/2006 |
| WO | 2006052927 A2 | 5/2006 |
| WO | 2006110275 A2 | 10/2006 |
| WO | 2007080974 A1 | 7/2007 |
| WO | 2007104397 A1 | 9/2007 |

* cited by examiner

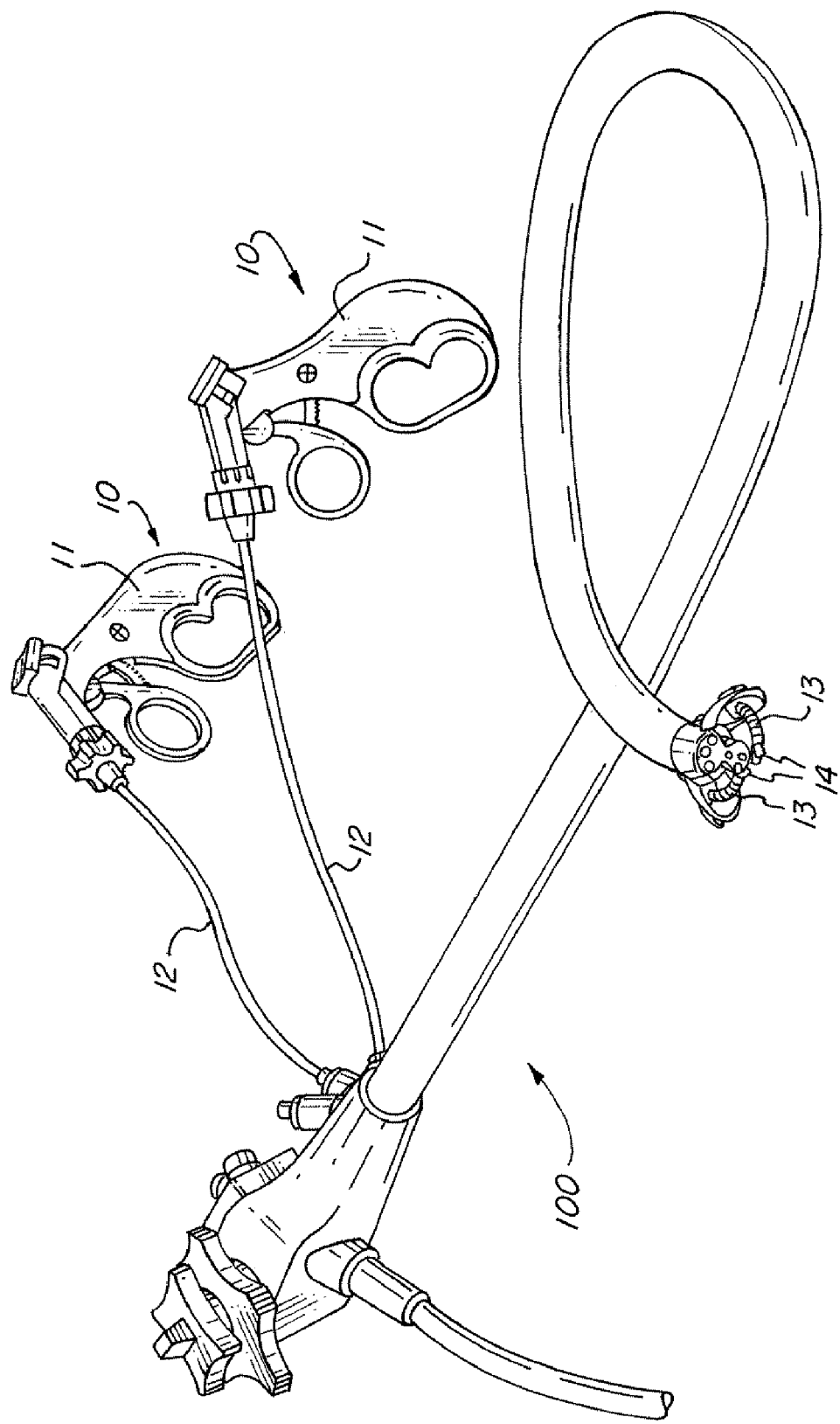

ARTICULATING ENDOSCOPE INSTRUMENT

FIELD OF THE INVENTION

The present invention relates to an endoscopic surgical instrument. In particular, the present invention relates to an endoscopic surgical instrument for use in, for example, transgastric or transluminal surgical techniques.

BACKGROUND OF THE INVENTION

The traditional method of surgery involves creating an incision in a patient large enough so that the surgeon can work with and handle directly the patient's organs and tissues. Unfortunately, this traditional method carries with it a relatively high risk of infection due to the exceptional amount of exposure to which the patient's internal organs and tissues are subjected during the surgery. Other significant drawbacks associated with traditional methods of surgery are the length of recovery time required for a patient and the significant pain suffered by the patient because of the size of the incision.

These negative effects of surgical treatment were significantly mitigated by the introduction of endoscopic surgery. Endoscopic surgery generally involves making one or more relatively small incisions in a patient and then inserting one or more small surgical tools. The surgical tools are generally mounted on one end of a long, thin element having on the other end a handle and a means for actuating or manipulating the surgical tool. The endoscopic surgical tools are often also outfitted with optical and light-delivery channels so that the surgeon can view the area of the surgery.

While the advent of endoscopic surgical techniques significantly reduced the drawbacks of traditional surgical techniques, endoscopic surgery still involves a relatively high risk of infection, a relatively long recovery period, and significant pain for the patient. Recently, these negative effects have been even further reduced by the introduction of transgastric and transluminal endoscopic surgery.

In transgastric surgery, for example, an endoscopic instrument is inserted into the patient's mouth and fed to the patient's stomach. The wall of the patient's stomach can then be punctured so that the instrument can access other parts of the patient's abdomen. An incision in the wall of the stomach is preferable to external incisions because there are no nerve endings in the stomach. Transgastric endoscopic surgery reduces patient pain and recovery time as well as the risk of infection.

An endoscopic instrument that is inserted into the patient for transgastric or transluminal surgery generally includes one or more surgical tools, an optical channel, one or more light channels, and/or one or more channels for evacuation or insufflation. The endoscopic instruments preferably have other unique features. A full description of the functioning of a transgastric/transluminal surgical apparatus can be found in commonly owned U.S. application Ser. No. 11/739,833, the disclosure of which is incorporated by reference herein. First, transgastric/transluminal surgical apparatuses preferably are designed such that insertion into the patient's body is easy and causes the patient a minimum of trauma. Second, the endoscopic instrument preferably provides a means for multiple surgical tools to be used to exert force or perform functions in multiple directions at the surgical site. This is more difficult in transgastric and transluminal surgery because there is only one possible angle of approach since the surgical tools are preferably inserted in the same place, for example, the patient's mouth. In conventional endoscopic surgery on the other hand, surgical tools can be inserted into multiple incisions at multiple locations in the abdomen so that the surgeon has an advantageous 'working triangle.' The working triangle allows the surgeon to exert force in multiple directions and therefore better perform surgical tasks. In transgastric and transluminal surgery, it is more difficult to create this working triangle since the surgical tools are inserted parallel to one another.

In general, an endoscopic surgical instrument for use in transgastric, transluminal, or similar surgical techniques has a handle portion, an elongated middle portion, and a tool portion. The handle and tool portion are located on opposite ends of the middle portion, such that when the instrument is inserted into a patient, the tool portion is directed to the surgical site inside the patient's body while the handle remains outside the patient's body so that the surgeon may control the tool portion. The handle generally includes mechanisms for actuating the tool portion of the surgical instrument. There are many types of tool portions of surgical instruments which may be used in this way, for example, grasping jaws, clippers, scissors, and the like.

Once endoscopic surgical instruments are present at a surgical site, whether in a transgastric, transluminal, or other setting, it is necessary that the surgeon have the ability to precisely control or steer the surgical instruments. The tool portions should be capable of easy movement around the surgical site. Indeed, one of the most critical components of an effective and safe surgical operation is the ability of the surgeon to efficiently perform the desired surgical tasks. For this reason, the surgeon must be able to move the tool portions in a precise manner with as little restriction on the movement of the tool portion as possible.

There are many endoscopic surgical instruments in the prior art which are intended to provide a surgeon with as much control over the tool portion as possible. For example, U.S. Pat. No. 5,318,528 to Heaven et al. discloses a steerable surgical device having an inner tubular member and an outer tubular member. The tubular members are disposed coaxially and are rotatable relative to one another. At least one of the tubular members is pre-bent at its distal end. When both tubular members are pre-bent, the distal end can be steered by rotating the tubular members relative to one another, so that the distal end is moved from between about a 90° configuration to a straight configuration relative to the axis of the tubular members. The configuration, or overall bend, of the distal end is changed as a result of the varying force of the pre-bent sections of the tubular members on each other as the tubular members are rotated. A surgical tool is mounted on a distal end of the inner tubular member and is operated by control wires.

Unfortunately, this design has significant drawbacks. For example, due to the fact that some flexibility is required in the tubular members at their distal end to change the configuration or overall bend of the distal end, the distal end is susceptible to unwanted flexing when a force is applied to the end. If a surgeon desires to exert a pulling or pushing force on a patient's body tissue, the device disclosed in Heaven et al. may not retain the desired curvature at its distal end. Such a situation introduces imprecision and uncertainty into the surgical procedure.

U.S. Pat. No. 5,921,915 to Aznoian et al. discloses a surgical instrument having a flexible body insertion tube and a tubular member having a sheath and forceps jaws (or other surgical instrument) attached at a distal end. The tubular member is disposed inside and slideable within the sheath, which is relatively stiff. The tubular member has at least one resilient bend near its distal end such that when the tubular member is forced out of the end of the sheath, the surgical instrument on the distal end will be deflected away from the axis of the sheath. The tubular member may be rotated about its longitudinal axis.

The surgical instrument disclosed in Aznoian et al. also suffers from significant drawbacks. First, due to the flexible nature of the tubular member, it may also flex in an undesirable manner when the surgeon exerts a pulling or pushing force with the tubular member. Second, the amount of control that a surgeon has over the distal end of the tubular member is limited because the amount of bend is fixed by the resilient bend. While the amount of bend may be controlled somewhat by the degree to which the distal end is protruded from the sheath, this amount of control over the surgical tool may not be adequate for some applications. Finally, actuation of the instrument's functions is complicated, such that it would require two hands to control the longitudinal displacement of the tubular member and the rotation of the tubular member.

U.S. Pat. No. 5,766,196 to Griffiths discloses a medical instrument with a steerable distal end attached to an elongated middle section which is in turn attached to a handle assembly. A surgical tool is mounted at the tip of the distal end. Control wires run from a steering knob located on the handle assembly through the middle section to the steerable distal end. The steerable distal end is comprised of stacked, disc-shaped elements which have holes for receiving the control wires, a central cavity, and two cut out portions which form a projection. The distal end is steered by tensioning the control wires such that the disc-shaped elements rock about their projections in unison. The distal end is therefore moveable in a plane to either side of the longitudinal axis of the elongated middle section. The distal end is rotatable into any desired angular position. A control and restraining mechanism holds the control wires and therefore the steerable section in a position selected by the surgeon.

The medical instrument disclosed in Griffiths also suffers from notable drawbacks. While the distal end allows articulation, the middle section to which the distal end is attached is a rigid, elongated member. The fact that the middle section is rigid limits the usefulness of the device in certain endoscopic surgery techniques. Particularly, transgastric and transluminal surgery require that the tools employed have at least some flexibility. Second, articulation of the distal end and actuation of the surgical tool would require use of two hands for accurate control.

What is needed, therefore, is an endoscopic surgical instrument that gives a surgeon precise control over the position of a surgical tool at a surgical site. The instrument should be employable and useful in a wide variety of surgical techniques. The instrument should also be simple and efficient to operate. It is also important that the instrument be easy to clean and sterilize. The instrument should also be simple to manufacture.

SUMMARY OF THE INVENTION

It is an object of the present invention to provide an endoscopic surgical instrument that gives a surgeon precise control over the position of a surgical tool at a surgical site.

It is a further object of the present invention to provide an endoscopic surgical instrument which is employable and useful in a wide variety of surgical techniques.

It is yet a further object of the present invention to provide an endoscopic surgical instrument which is simple and efficient to operate.

It is still a further object of the present invention to provide an endoscopic surgical instrument which is easy to clean and sterilize.

It is yet another object of the present invention to provide an endoscopic surgical instrument which is simple to manufacture.

These and other objects are accomplished according to one embodiment of the present invention by provision of an endoscopic surgical instrument which includes a handle portion on a proximal end of the endoscopic surgical instrument, an elongated middle portion having a length and comprising a proximal end which is coupled to the handle portion, an articulating portion coupled to a distal end of the elongated middle portion which includes a plurality of link members coupled together such that the articulating portion is bendable in a plane, and a tool portion on a distal end of the endoscopic surgical instrument, coupled to a distal end of the articulating portion. The elongated middle portion consists of components which extend along substantially the entire length of the middle portion that are formed of flexible materials.

In some embodiments, the elongated middle portion includes at least one lumen along its length and the tool portion is coupled to a tool insert disposed in the elongated middle portion, and the tool insert is coupled at its proximal end to a lever member disposed on the handle portion such that movement of the lever member exerts a force on the tool insert to actuate the tool portion. In some embodiments, the tool insert and tool portion are removable as a unit and replaceable with one of a plurality of other tool insert and tool portion units having different configurations.

In some embodiments, the handle portion includes a lever lock mechanism which engages a notched portion of the lever member and locks the lever member in a selected position. In some embodiments, the lever member includes a friction-enhancing coating on a portion thereof to reduce unwanted movement of the lever member. In some embodiments, the tool insert is adapted to conduct electricity to the tool portion from a power source which is coupled to the proximal end of the tool insert.

In some embodiments, the endoscopic surgical instrument further comprises two control wires disposed in the elongated middle portion each coupled to an articulation control member disposed on the handle portion and coupled to the distal end of the articulating portion and wherein the articulation control member is movable in a plane and such movement controls the bending of the articulating portion. In some embodiments, the control wires and the articulation control member are connected to a drum which is rotatably connected to the handle portion. In some embodiments, a drum is rotatably connected to the handle portion, and the control wires and the articulation control member are connected to the drum such that movement of the articulation control member causes rotation of the drum in the plane of movement of the articulation control member, thereby exerting force on the control wires. In some embodiments, the plane of movement of the articulation control member substantially corresponds to the plane of movement of the bending of the articulating portion.

In some embodiments, the handle portion includes a slide lock mechanism which frictionally engages the articulation control member and locks the articulation control member in a selected position. In some embodiments, the articulation control member includes a friction-enhancing coating on a portion thereof to reduce unwanted movement of the articulation control member. In some embodiments, the articulation control member is accessible by a thumb of a user of the endoscopic surgical instrument and the lever member is simultaneously accessible by a finger of a user of the endoscopic surgical member.

In some embodiments, the tool insert is also coupled to a rotating control member which transmits rotation about the longitudinal axis of the elongated middle portion to the tool insert which in turn rotates the tool portion relative to the articulating portion. In some embodiments, the rotating control member rotates in increments among a selected number of fixed positions. In some embodiments, the rotating control member includes a friction-enhancing coating on a portion thereof to reduce unwanted movement of the rotating control member. In some embodiments, the handle portion includes a rotation lock mechanism which frictionally engages the rotating control member and locks the rotating control member in a selected position.

In some embodiments, the lever member, the lever lock mechanism, the articulation control member, the slide lock mechanism, the rotating control member, and the rotating lock mechanism are accessible by a single hand of a user of the endoscopic surgical instrument. In some embodiments, the endoscopic surgical instrument is adapted for use by both a left hand alone and a right hand alone of a user of the endoscopic surgical instrument. In some embodiments, the endoscopic surgical instrument is substantially sealed. In some embodiments, the endoscopic instrument is used for the transmission of fluid matter to or from a surgical site.

According to another embodiment of the present invention, an endoscopic surgical instrument is provided, which includes a handle portion on a proximal end of the endoscopic surgical instrument, an elongated middle portion having a length and comprising a proximal end which is coupled to the handle portion and at least one lumen along its length, an articulating portion coupled to a distal end of the elongated middle portion including a plurality of link members coupled together such that the articulating portion is bendable in a plane, a tool portion on a distal end of the endoscopic surgical instrument, coupled to a distal end of the articulating portion. Two control wires are each disposed in the elongated middle portion, and the two control wires are coupled to an articulation control member disposed on the handle portion. The two control wires are coupled to the distal end of the articulating portion and the articulation control member is movable in a plane and such movement controls the bending of the articulating portion. The middle portion consists of components which extend along substantially the entire length of the middle portion that are formed of flexible materials.

In some embodiments, the control wires and the articulation control member are connected to a drum which is rotatably connected to the handle portion. In some embodiments, a drum is rotatably connected to the handle portion, and the control wires and the articulation control member are connected to the drum such that movement of the articulation control member causes rotation of the drum in the plane of movement of the articulation control member, thereby exerting force on the control wires. In some embodiments, the plane of movement of the articulation control member substantially corresponds to the plane of movement of the bending of the articulating portion.

In some embodiments, the handle portion includes a slide lock mechanism which frictionally engages the articulation control member and locks the articulation control member in a selected position. In some embodiments, the articulation control member includes a friction-enhancing coating on a portion thereof to reduce unwanted movement of the articulation control member.

In some embodiments, the tool portion is coupled to a tool insert disposed in the elongated middle portion, and the tool insert is coupled at its proximal end to a lever member disposed on the handle portion such that movement of the lever member exerts a force on the tool insert to actuate the tool portion. In some embodiments, the tool insert and tool portion are removable as a unit and replaceable with one of a plurality of other tool insert and tool portion units having different configurations. In some embodiments, the handle portion includes a lever lock mechanism which engages a notched portion of the lever member and locks the lever member in a selected position. In some embodiments, the lever member includes a friction-enhancing coating on a portion thereof to reduce unwanted movement of the lever member.

In some embodiments, the articulation control member and the lever member are disposed on the handle portion so as to be simultaneously accessible by a single hand of a user of the endoscopic surgical instrument. In some embodiments, the tool insert is adapted to conduct electricity to the tool portion from a power source which is coupled to the proximal end of the tool insert.

In some embodiments, the tool insert is also coupled to a rotating control member which transmits rotation about the longitudinal axis of the elongated middle portion to the tool insert which in turn rotates the tool portion relative to the articulating portion. In some embodiments, the rotating control member rotates in increments among a selected number of fixed positions. In some embodiments, the rotating control member includes a friction-enhancing coating on a portion thereof to reduce unwanted movement of the rotating control member. In some embodiments, the handle portion includes a rotation lock mechanism which frictionally engages the rotating control member and locks the rotating control member in a selected position.

In some embodiments, the endoscopic surgical instrument is adapted for use by both a left hand alone and a right hand alone of a user of the endoscopic surgical instrument. In some embodiments, the endoscopic surgical instrument is substantially sealed. In some embodiments, the endoscopic surgical instrument is used for the transmission of fluid matter to or from a surgical site.

According to a third embodiment of the present invention, an endoscopic surgical instrument is provided, which includes a handle portion on a proximal end of the endoscopic surgical instrument, an elongated middle portion having a length and comprising a proximal end which is coupled to the handle portion and at least one lumen along its length, and an articulating portion coupled to a distal end of the elongated middle portion including a plurality of link members coupled together such that the articulating portion is bendable in a plane. Two control wires are each disposed in the elongated middle portion, wherein the two control wires are coupled to an articulation control member disposed on the handle portion and are coupled to the distal end of the articulating portion and wherein the articulation control member is movable in a plane and such movement controls the bending of the articulating portion. A tool insert is disposed in the elongated middle portion which includes a tool portion coupled to a distal end of the articulating portion, and the tool insert is coupled at its proximal end to a lever member disposed on the handle portion. Movement of the lever member exerts a force on the tool insert to actuate the tool portion. The articulation control member and the lever member are disposed on the handle portion so as to be simultaneously accessible by a single hand of a user of the endoscopic surgical instrument. The middle portion consists of components which extend along substantially the entire length of the middle portion that are formed of flexible materials.

In some embodiments, the control wires and the articulation control member are connected to a drum which is rotatably connected to the handle portion. In some embodiments, a drum is rotatably connected to the handle portion, and the control wires and the articulation control member are connected to the drum such that movement of the articulation control member causes rotation of the drum in the plane of movement of the articulation control member, thereby exerting force on the control wires. In some embodiments, the plane of movement of the articulation control member substantially corresponds to the plane of movement of the bending of the articulating portion.

In some embodiments, the tool insert is also coupled to a rotating control member which transmits rotation about the longitudinal axis of the elongated middle portion to the tool insert which in turn rotates the tool portion relative to the articulating portion. In some embodiments, the rotating control member rotates in increments among a selected number of fixed positions. In some embodiments, the articulation control member includes a friction-enhancing coating on a portion thereof to reduce unwanted movement of the articulation control member. In some embodiments, the lever member includes a friction-enhancing coating on a portion thereof to reduce unwanted movement of the lever member. In some embodiments, the rotating control member includes a friction-enhancing coating on a portion thereof to reduce unwanted movement of the rotating control member.

In some embodiments, the handle portion includes a slide lock mechanism which frictionally engages the articulation control member and locks the articulation control member in a selected position. In some embodiments, the handle portion includes a lever lock mechanism which engages a notched portion of the lever member and locks the lever member in a selected position. In some embodiments, the handle portion includes a rotation lock mechanism which frictionally engages the rotating control member and locks the rotating control member in a selected position.

In some embodiments, the lever member, the lever lock mechanism, the articulation control member, the slide lock mechanism, the rotating control member, and the rotating lock mechanism are accessible by a single hand of a user of the endoscopic surgical instrument. In some embodiments, the endoscopic surgical instrument is adapted for use by both a left hand alone and a right hand alone of a user of the endoscopic surgical instrument. In some embodiments, the endoscopic surgical instrument is substantially sealed. In some embodiments, the tool insert and tool portion are removable as a unit and replaceable with one of a plurality of other tool insert and tool portion units having different configurations. In some embodiments, the endoscopic surgical instrument is used for the transmission of fluid matter to or from a surgical site.

According to a fourth embodiment of the present invention, an endoscopic surgical instrument is provided, which includes a handle portion on a proximal end, an elongated middle portion having a length comprising a proximal end which is coupled to the handle portion and at least one lumen along its length, an articulating portion coupled to a distal end of the elongated middle portion, and a tool portion on a distal end of the endoscopic surgical instrument, coupled to a distal end of the articulating portion. The elongated middle portion consists of components which extend along substantially the entire length of the middle portion that are formed of flexible materials. The articulating portion comprises a plurality of link members coupled together such that the articulating portion is bendable in a plane. Two control wires are each disposed in the elongated middle portion, and the two control wires are coupled to an articulation control member disposed on the handle portion. The two control wires are coupled to the distal end of the articulating portion. The articulation control member is movable in a plane and such movement controls the bending of the articulating portion. The plane of movement of the articulation control member substantially corresponds to the plane of movement of the bending of the articulating portion.

In some embodiments, the tool portion is coupled to a tool insert disposed in the elongated middle portion, and the tool insert is coupled at its proximal end to a lever member disposed on the handle portion such that movement of the lever member exerts a force on the tool insert to actuate the tool portion. In some embodiments, the tool insert and tool portion are removable as a unit and replaceable with one of a plurality of other tool insert and tool portion units having different configurations. In some embodiments, the articulation control member and the lever member are disposed on the handle portion so as to be simultaneously accessible by a single hand of a user of the endoscopic surgical instrument.

In some embodiments, the control wires and the articulation control member are connected to a drum which is rotatably connected to the handle portion. In some embodiments, a drum is rotatably connected to the handle portion, and the control wires and the articulation control member are connected to the drum such that movement of the articulation control member causes rotation of the drum in the plane of movement of the articulation control member, thereby exerting force on the control wires. In some embodiments, the plane of movement of the articulation control member substantially corresponds to the plane of movement of the bending of the articulating portion.

In some embodiments, the tool insert is also coupled to a rotating control member which transmits rotation about the longitudinal axis of the elongated middle portion to the tool insert which in turn rotates the tool portion relative to the articulating portion. In some embodiments, the rotating control member rotates in increments among a selected number of fixed positions. In some embodiments, the articulation control member includes a friction-enhancing coating on a portion thereof to reduce unwanted movement of the articulation control member. In some embodiments, the lever member includes a friction-enhancing coating on a portion thereof to reduce unwanted movement of the lever member. In some embodiments, the rotating control member includes a friction-enhancing coating on a portion thereof to reduce unwanted movement of the rotating control member.

In some embodiments, the handle portion includes a slide lock mechanism which frictionally engages the articulation control member and locks the articulation control member in a selected position. In some embodiments, the handle portion includes a lever lock mechanism which engages a notched portion of the lever member and locks the lever member in a selected position. In some embodiments, the handle portion includes a rotation lock mechanism which frictionally engages the rotating control member and locks the rotating control member in a selected position. In some embodiments, the lever member, the lever lock mechanism, the articulation control member, the slide lock mechanism, the rotating control member, and the rotating lock mechanism are accessible by a single hand of a user of the endoscopic surgical instrument.

In some embodiments, the endoscopic surgical instrument is adapted for use by both a left hand alone and a right hand alone of a user of the endoscopic surgical instrument. In some embodiments, the endoscopic surgical instrument is substantially sealed. In some embodiments, the endoscopic surgical instrument is used for the transmission of fluid matter to or from a surgical site.

Other objects, features, and advantages will be apparent from the following detailed description of embodiments of the present invention taken in conjunction with the accompanying drawings.

BRIEF DESCRIPTION OF THE DRAWINGS

FIG. 1A is an isometric view of a transgastric/transluminal endoscopic surgery apparatus with two endoscopic surgical instruments of FIG. 1 inserted therein.

DETAILED DESCRIPTION OF THE DRAWINGS

Figure 1:
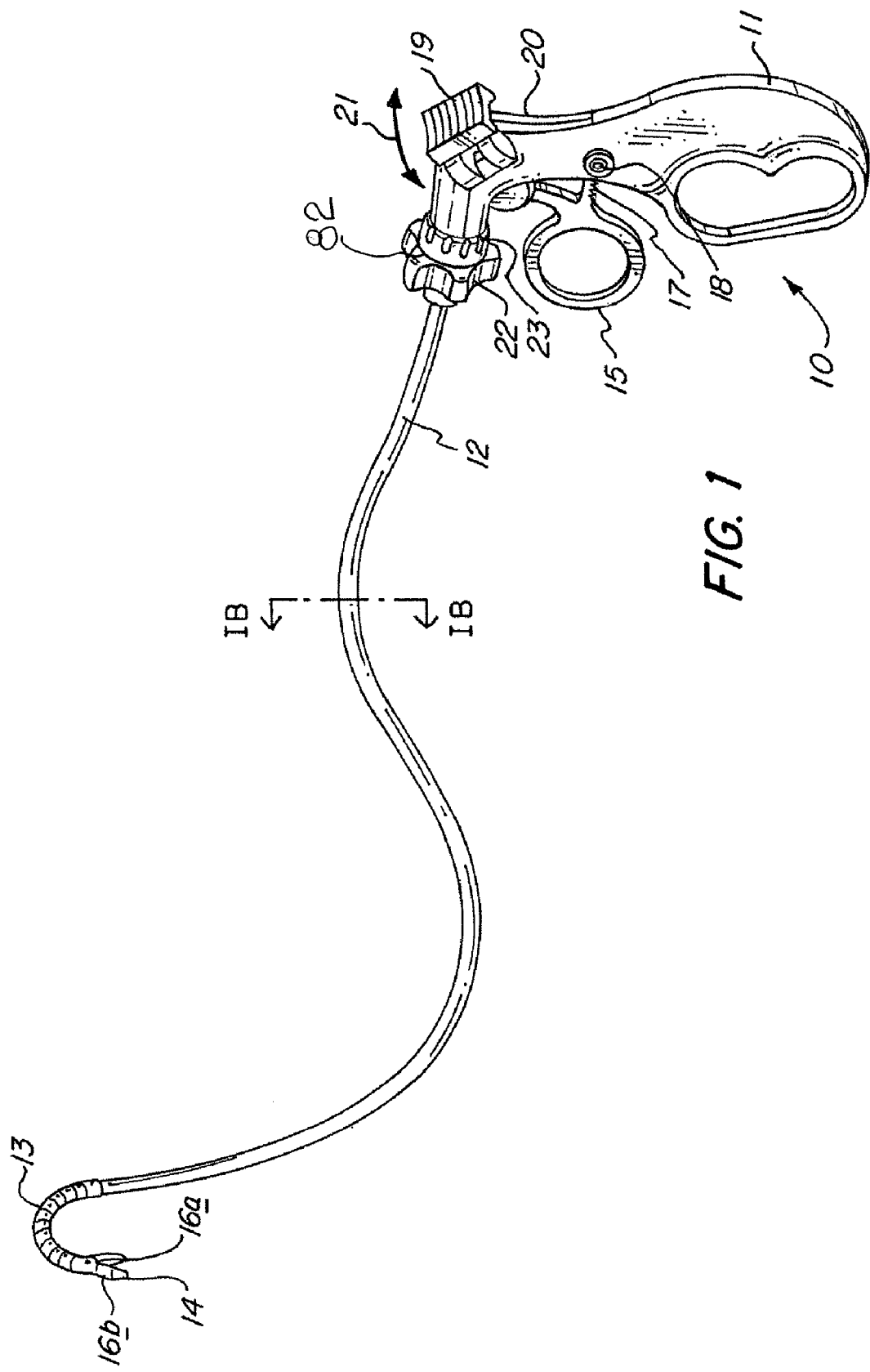
FIG. 1 is an isometric view of an endoscopic surgical instrument according to an embodiment of the present invention.

The invention will now be described in reference to the drawings, which show embodiments of the present invention. FIG. 1 shows an endoscopic surgical instrument 10 according to one exemplary embodiment of the present invention. The surgical instrument 10 includes a handle portion 11, an elongated middle portion 12, an articulating portion 13, and a tool portion 14. Throughout this application, the "distal" end of the surgical instrument 10 shall be the end having the tool portion 14 and the "proximal" end of the surgical instrument 10 shall be the end having the handle portion 11. This relationship shall also apply in references made to the various components of the surgical instrument 10.

The handle portion 11 of the surgical instrument 10 is ergonomically designed for comfortable use by a surgeon. The handle portion 11 is designed symmetrically so that it is comfortably grasped and operated by either a left hand or a right hand. This feature allows a surgeon to use two surgical instruments 10 simultaneously. Such an arrangement is shown in FIG. 1A, which shows a transgastric/transluminal surgery apparatus 100. Two surgical instruments 10 are inserted into lumens of the apparatus 100 which is inserted as a whole into a body cavity of a patient. The articulating portion 13 and the tool portion 14 are shown protruding from the distal end of the apparatus 100. Using this arrangement, a surgeon easily controls two surgical instruments simultaneously. While this is one application of the endoscopic surgical instruments of the present invention, the instruments are used in a variety of other situations and with a variety of other equipment. The surgery apparatus 10 is merely an example of one application of the present invention.

The handle portion 11 includes control mechanisms for all of the functions of the surgical instrument 10. Lever member 15 controls the actuation of the tool portion 14. In the embodiment shown in FIGS. 1 and 1A, the tool portion 14 is a grasper-type tool for securely grasping and holding tissue or other materials or objects between its two movable jaw members 16a and 16b. The jaw members 16a and 16b are moved by moving the lever 15, which, in the embodiment shown in FIG. 1, has a ring portion for receiving the index or middle finger of the surgeon. In effect, the lever 15 has a trigger-like action.

In the embodiment shown in FIG. 1, the tool portion 14 is coupled to the lever 15 by a tool insert (not visible in FIG. 1). The term 'tool insert' as used herein encompasses multiple designs and means for coupling the tool portion to the lever or other mechanism for receiving an input force and actuating the tool portion, and is not to be limited to the designs and embodiments disclosed in the drawings and this description. As described below in further detail, some embodiments of the present invention include tool inserts which incorporate the tool portion and mechanisms for actuating the tool and coupling it to the lever 15 into a single unit. These tool inserts are easily removed and replaced by tool inserts having a differently configured tool portion. In other embodiments, both the tool insert and the tool portion are embedded in the instrument 10, and the tool insert comprises an actuation member for linking the tool portion to the lever member and transmitting force from the lever to the tool portion. The tool insert in such embodiments is simply a metal wire. In either embodiment, the tool insert may be flexed along its longitudinal axis in the presence of a radial force but does not permit compression or lengthening as a result of forces along its axis. This allows the lever 15 to transmit pushing and pulling forces to the tool portion 14 via the tool insert while still enabling the surgical instrument 10 to be bendable.

The handle portion 11 shown in FIG. 1 also includes a locking mechanism for locking the lever 15, and thus the tool portion 14, into a position selected by the surgeon. The locking mechanism includes a notched portion 17 attached to the lever 15. The notched portion 17 slides in and out of the handle portion 11 as the lever 15 is moved. The locking mechanism further includes a rod or other member on the inside of handle portion 11 which is able to engage or disengage the notches of the notched portion 17 by movement of the button 18 on the handle portion 11. The surgeon is able to alternate the button 18 between a depressed and non-depressed position so as to lock the lever 15, and thus the position of the tool portion 14, as he or she desires during the surgery.

Handle portion 11, as shown in FIG. 1, further includes an articulation control 19 which is used to control the articulation of the articulating portion 13. The articulation control 19 shown in FIG. 1 moves in a single plane indicated by the arrow 21. Such single plane movement of the articulation control 19 corresponds to the single plane movement of the articulating section 13, which is described in detail below. The articulation control 19 and the articulating portion 13 are coupled by control wires. This coupling relationship is described in detail below. The articulation control 19 is disposed on handle portion 11 so that the surgeon accesses it with his or her thumb, while still being able to maintain his or her grip on the handle portion 11 and to actuate the lever 15. It is therefore very simple to actuate both the tool portion 14 and the articulating portion 13 simultaneously.

Articulation control 19 is selectively locked into position by a slide lock mechanism 20. Slide lock mechanism 20 is also accessible by the surgeon's thumb. In the embodiment shown in FIG. 1, the slide lock mechanism 20 is slideable up and down the proximal end of the handle portion 11. When it is moved up to the engaged position, the slide lock mechanism 20 engages a lower surface of the articulation control 19, such as by frictional engagement. In this way it prevents the articulation control 19 from moving unexpectedly or undesirably and thereby locks the articulating portion 13 in position. When the slide lock mechanism 20 is moved down the proximal end of the handle portion 11 and disengages the lower surface of the articulation control 19, the articulation control 19 is freely movable. In some embodiments, the articulation control 19 includes notches on a lower surface for engaging with a protrusion on the slide lock mechanism 20. In other embodiments, the articulation control 19 includes notches on an upper surface for engaging with a protrusion on a slide lock mechanism which is positioned on the handle portion 11 above the articulation control 19.

The handle portion 11 further includes a rotating control 22 which is also coupled to the tool insert which links the lever 15 and the tool portion 14. The rotating control 22 is coupled to the tool insert so that when the rotating control 22 is rotated by the surgeon, the rotation is transmitted via the tool insert to the tool portion 14. In this way the tool portion 14 may be rotated independently of the articulating portion 13.

In some embodiments, the rotating control 22 is designed to rotate in increments among a selected number of fixed positions. For example, in some embodiments, the rotating control 22 is designed so that the rotating control will 'click' at 10° rotational increments when it is rotated. The increments are determined by the use of, for example, detents on an inner part of the rotating control or a surface of the handle. This 'staging' feature allows a user to ensure a desired amount of rotation of the tool portion.

The rotating control 22 may also be locked into position by the rotation lock mechanism 23. The rotation lock mechanism 23 is disposed on threads which allow it to move when it is rotated from a proximal position separated from the rotating control to a distal position in which it makes frictional contact with the rotating mechanism. When the rotation lock mechanism 23 is moved into its distal position it frictionally engages the rotating control 22 so as to prevent relative rotation between the rotating control 22 and the handle portion 11. This allows the surgeon to select a position for the tool portion 14 by rotating the rotating control 22 and then locking the tool portion 14 into position with the rotation lock mechanism 23. The rotating control 22 includes, in some embodiments, a friction-enhancing coating 82 on a portion thereof. Both the rotating control 22 and the rotation lock mechanism 23 are accessible by the surgeon's index finger.

Thus, all of the controls of the surgical instrument 10 are accessible by a single hand of the surgeon. The surgeon is not required to release his or her grip on the handle portion 11 to access the controls. When the surgeon grips the handle portion 11, the lever 15 is actuated by the surgeon's middle finger. The button 18 for locking the lever 15 in position is accessible by the surgeon's thumb. The articulation control 19 and the slide lock mechanism 20 are also accessible by the surgeon's thumb. Finally, the rotating control 22 and the rotation lock mechanism 23 are accessible by the surgeon's index finger. The surgeon can therefore precisely steer the tool portion around a surgical site.

Figure 1B:
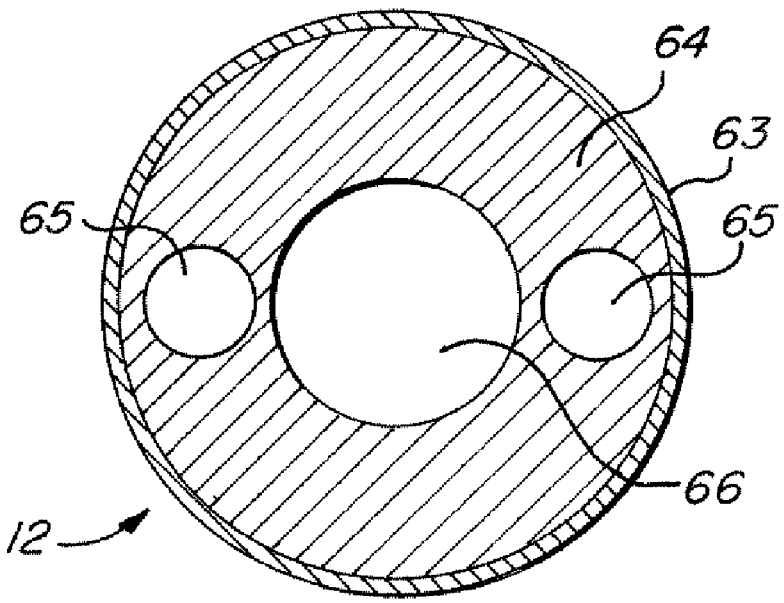
FIG. 1B is a cross-section view of the endoscopic surgical instrument of FIG. 1 taken along line IB-IB.

FIG. 1B shows a cross-section of an elongated middle portion 12 of an endoscopic surgical instrument 10 according to an embodiment of the present invention. The elongated middle portion 12 connects the handle portion 11 and the articulating portion 13. In the embodiment shown in FIGS. 1, 1A, and 1B, the middle portion 12 has an outer sheath 63 which is made of flexible, biocompatible material. The outer sheath 63 surrounds an inner part 64. The middle portion 12 is designed and constructed to be highly resistant to twisting along its length. The inner part 64 has lumens 65 and 66 which run along its length from the handle portion 12 to the articulating portion 13. The lumens 65 are designed to accommodate the control wires which link the articulation control 19 and the articulating portion 13. The lumen 66 is designed to accommodate the tool insert which links the lever 15 and the tool portion 14. The lumens 65 and 66 align with openings in the link members of the articulating portion (as described below) so that the tool inserts run along the length of the instrument. Other suitable designs for the elongated middle portion are appropriate for use in the present invention. A coiled, metal wire sheath is employed in some embodiments as the outer sheath 63. Proper functioning of the endoscopic surgical instruments according to the present invention, however, require that the middle portion 12 be flexible and resilient to radial forces, yet substantially incompressible or deformable when subjected to axial forces. These features allow for the surgical instrument to be easily inserted into a surgical apparatus such as apparatus 100 and for the surgeon to effectively use pushing or pulling forces with the surgical instrument.

Figure 1C:
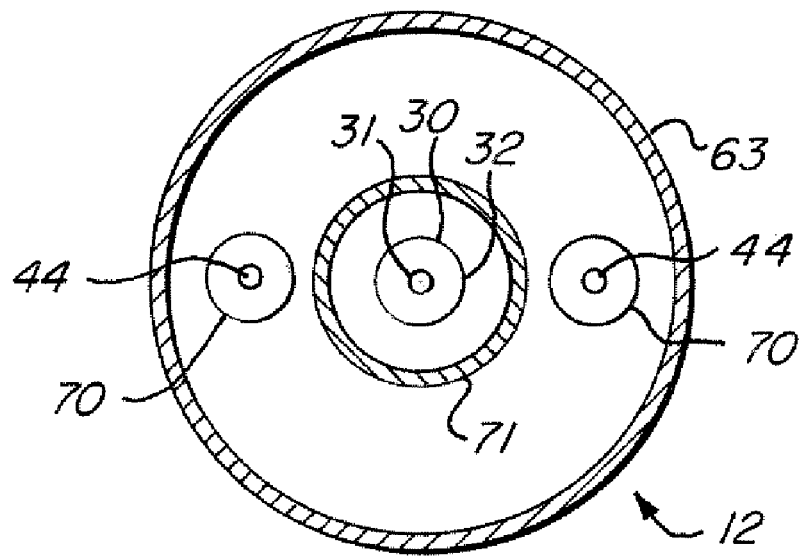
FIG. 1C is a schematic view of the cross-section of an endoscopic surgical instrument according to the present invention.

FIG. 1C shows a schematic view of a second cross-section of an elongated middle portion. As in FIG. 1B, the middle portion has an outer sheath 63 which is made of flexible, biocompatible material. In this embodiment, the sheath 63 is constructed of a material that is more resistant to pinching, which is necessary because of the absence of an inner part 64. FIG. 1C shows the tool insert 30 (described below) as well as the control wires 44 and their sheaths 70 (also described below). A teflon sheath 71 is also shown schematically which surrounds the tool insert 30 and prevents the various components contained in the middle portion from binding up with one another.

Figures 2, 2A:
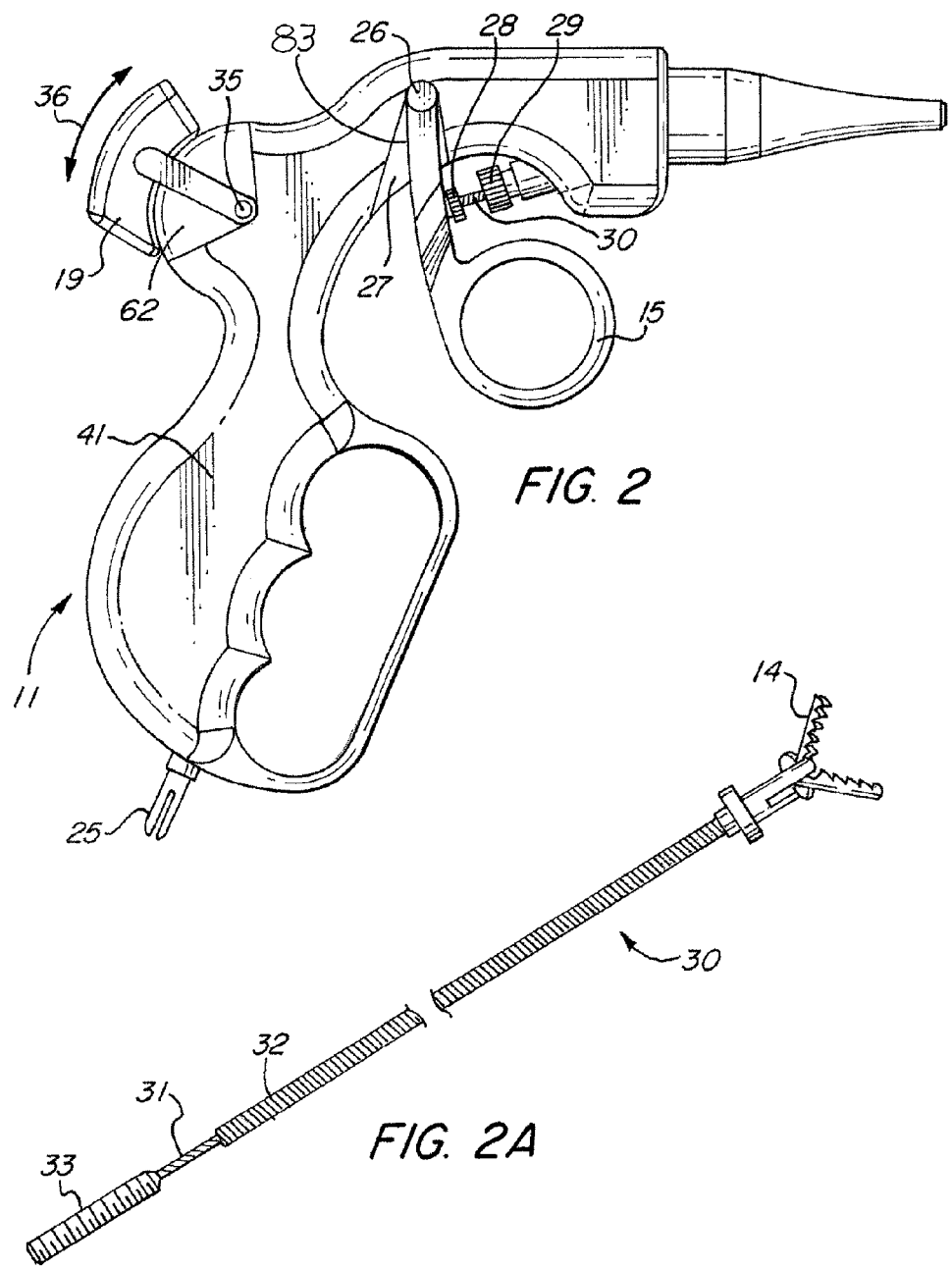
FIG. 2 is a side elevation view of a handle portion of an endoscopic surgical instrument according to an embodiment of the present invention.
FIG. 2A is a side elevation view of a tool portion and a tool insert of the endoscopic surgical instrument of FIG. 2.

FIG. 2 shows a handle portion 11 which is part of an endoscopic surgical instrument according to another embodiment of the present invention. The body of the handle portion 11 includes two plates, one of which, plate 41, is shown in FIG. 2. The handle portion 11 of FIG. 2 includes a lever 15 and a slide control 19. In the embodiment shown in FIG. 2, the handle portion 11 also includes a power input 25 which connects to an electrical power source. By the power input 25, the tool portion of the endoscopic surgical instrument is provided with electrical power for cutting and/or coagulating tissue and the like.

The handle portion 11 of the embodiment of FIG. 2 does not include a rotating control like the rotating control 22 shown in the embodiment of FIG. 1. The handle portion 11 of the embodiment of FIG. 2, therefore, is adapted such that the surgeon may use his or her index finger or middle finger to actuate the lever 15. The handle portion 11 of the embodiment of FIG. 2 is also designed so that the articulation control 19 is accessible by the surgeon's thumb. The embodiment shown in FIG. 2 is therefore also easily used by a single hand of a surgeon. The surgeon grips the handle portion 11, uses his or her finger on the lever 15, uses his or her thumb on the articulation control 19, and may actuate both controls without release his or her grip on the handle portion 11.

The handle portion 11 of the embodiment of FIG. 2 does not include locking mechanisms such as the lever lock mechanism, the slide lock mechanism 20, or the rotation lock mechanism 23 like the embodiment shown in FIG. 1. Instead, unwanted movement of the control parts, i.e. the lever 15 and the articulation control 19, is inhibited or reduced by friction. This feature is described in more detail below in reference to FIGS. 3 and 4. In some embodiments, friction-enhancing coating 83 is included on a portion of the lever 15.

The lever 15, which actuates the tool portion of the endoscopic surgical instrument, is pivotable about pivot 26 within the cut-out region 27 on the handle portion 11. A trigger anchor 28 is mounted on the lever 15, which couples with one end of a tool insert having its other end coupled to the tool portion. FIG. 2A shows a tool insert 30 which acts as the tool insert referenced above and links the lever 15 and the tool portion 14. The tool insert 30 has a wire portion 31 which is disposed inside a coiled wire sheath 32. The wire portion 31 is able to slide axially within the coiled wire sheath 32. Such sliding movement exerts a pulling or pushing force on the tool portion 14, located on the distal end of tool insert 30. The tool portion 14 is biased in either an open or closed position by a spring force which is overcome when the tool is actuated. The tool insert 30, like the middle portion 12, is flexible and resilient to radial forces but is substantially incompressible or deformable when subjected to axial force. The tool portion 14 is shown as a grasping tool with teeth in FIG. 2A. Many different types of tools may be used, such as scissors, clippers, hooks, and the like. On the proximal end of the tool insert 30 is a threaded portion 33.

The threaded portion 33 is received in the center of the trigger anchor 28 on the lever 15. The trigger anchor 28 also has an internal threaded portion to mate with the threaded portion 33 of the tool insert 30. In some embodiments, the tension of the wire 31 between the lever 15 and the tool portion 14 is adjusted by twisting the trigger anchor 28.

Figure 3:
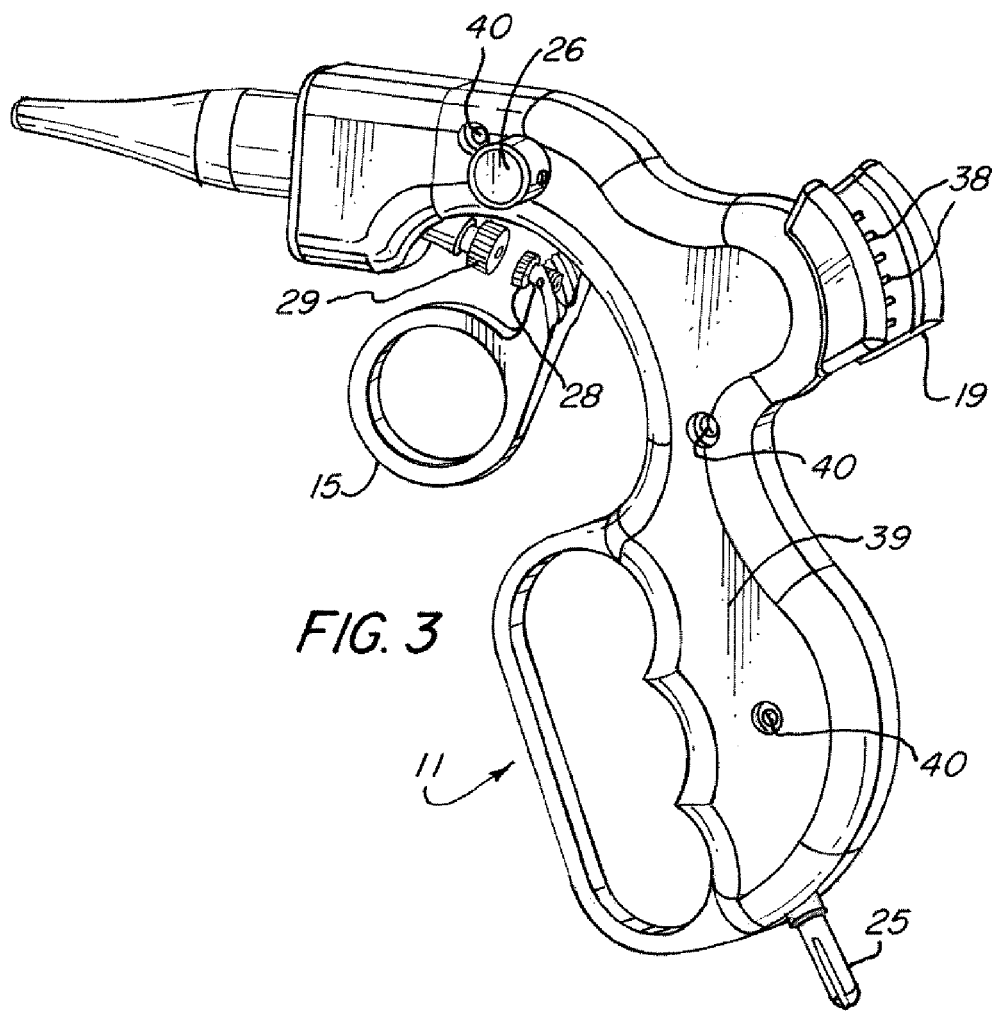
FIG. 3 is an isometric view of the handle portion of the endoscopic surgical instrument of FIG. 2.
Figure 4:
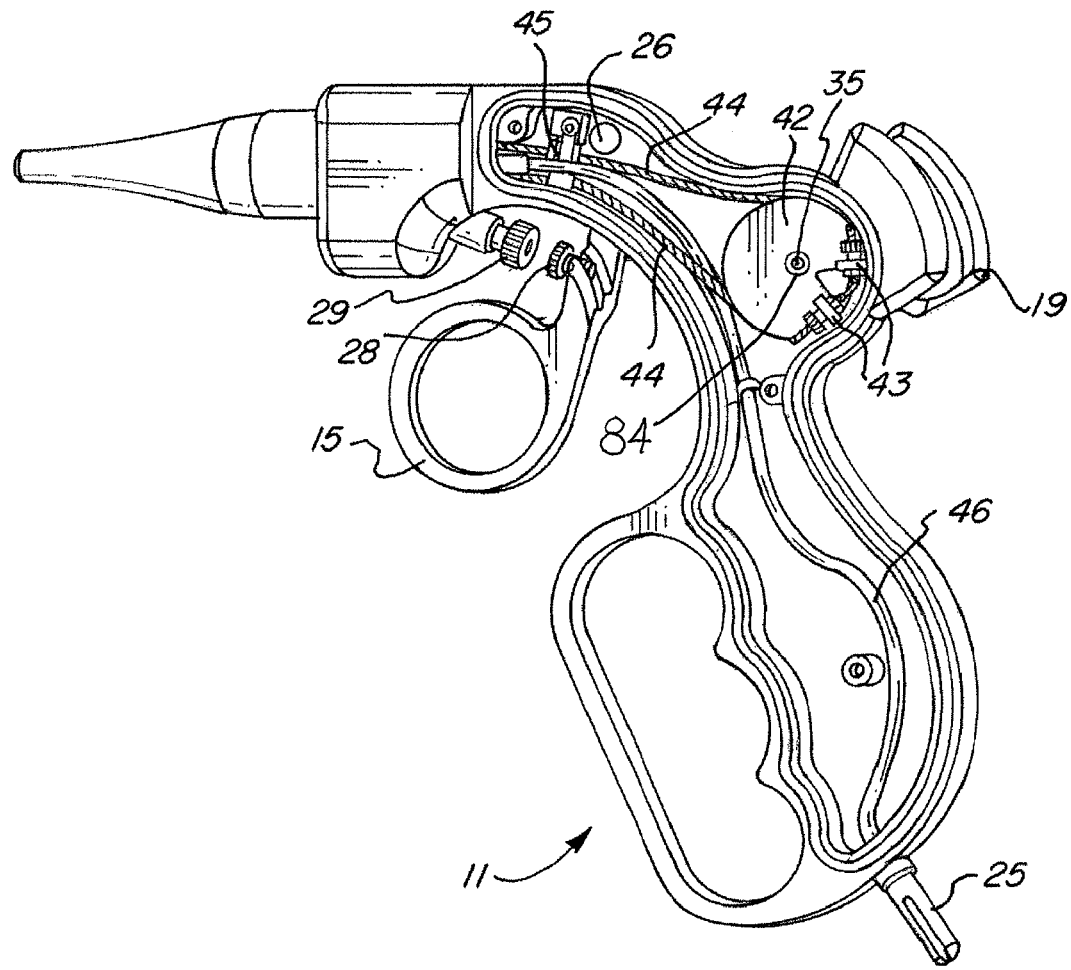
FIG. 4 is an isometric view of the interior of the handle portion of an endoscopic surgical instrument of FIG. 2.
Figure 5:
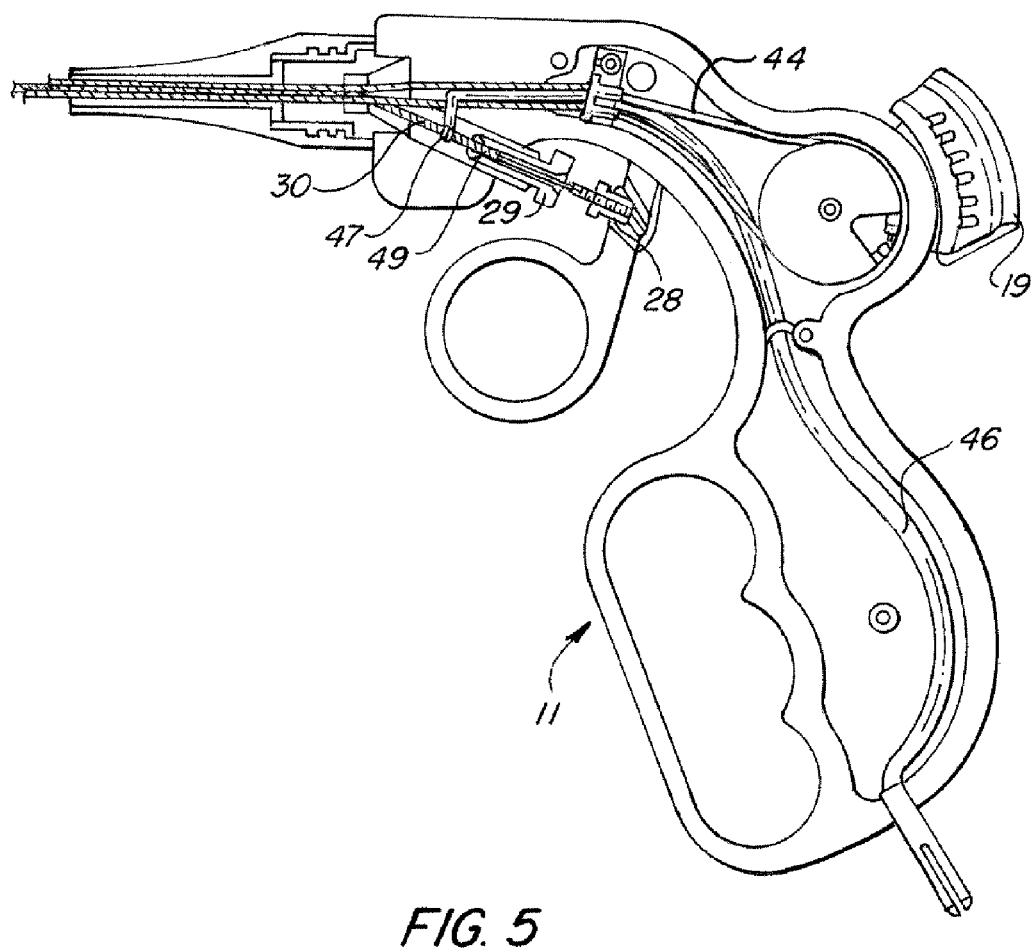
FIG. 5 is a cross-section view of the handle portion of the endoscopic surgical instrument of FIG. 2 taken along line V-V.
Figure 5A:
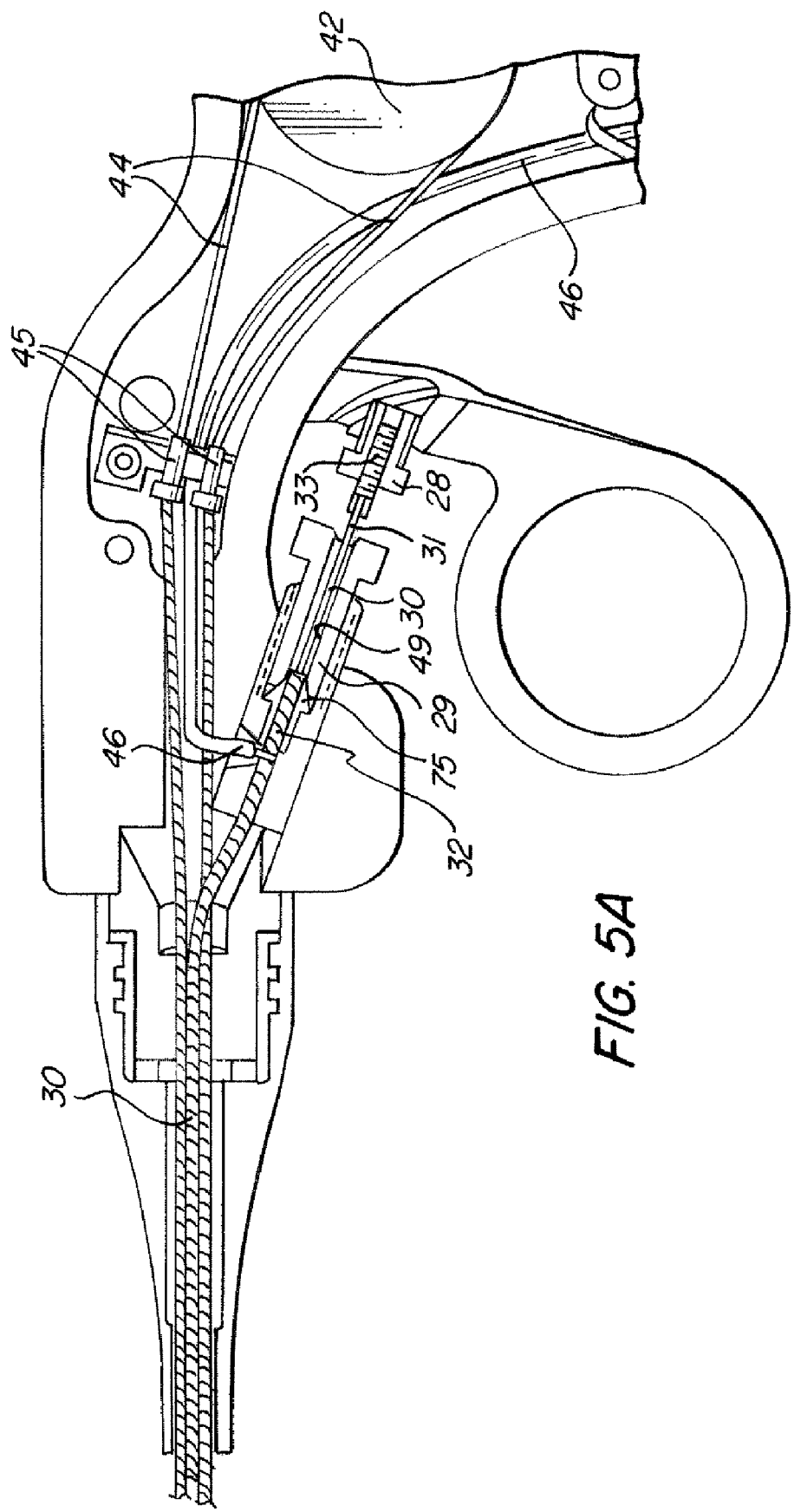
FIG. 5A is an enlarged view of the cross-section view of the handle portion of the endoscopic surgical instrument of FIG. 2 taken along line V-V shown in FIG. 5.

FIGS. 5 and 5A show cross-section views of the handle portion 11 of FIGS. 2, 3, and 4. An insulated electrical wire 46 is connected to the power input 25. The electrical wire 46 runs up the handle portion 11 to be coupled with the tool insert 30. In the embodiment shown in FIGS. 5 and 5A, the electrical wire 46 makes a conducting connection 47 with the inner clamp 75 portion of a tool insert clamp which conducts electricity to the tool insert 30. In the embodiment shown, electricity is not conducted to the lever 15 via the tool insert 30 and the trigger anchor 28 because a layer of heat shrink insulation is applied between the wire portion 31 and the threaded portion 33 of the tool insert 30. FIGS. 5 and 5A show the control wires 44 and the tool insert 30 exiting the handle portion 11 at its distal end.

FIG. 5 and particularly FIG. 5A show the manner in which the tool insert is coupled within the handle portion 11. The tool insert 30 is disposed in a channel 49. The threaded portion 33 of the tool insert 30 is shown connected to the trigger anchor 28. A tool insert clamp, comprising an outer clamp 29 and an inner clamp 75, secures the coiled wire sheath 32 and prevents it from moving within channel 49. Therefore, when lever 15 is moved, it exerts a pulling or pushing force on the wire portion 31 which slides within the coiled wire sheath 32.

In the embodiment shown in FIGS. 2, 2A, 3, 4, 5, the tool portion 14 as well as the tool insert 30 are easily removable from the surgical instrument 10. The tool insert 30, and thus the tool portion 14, is interchangeable with other tool inserts. This feature allows a surgeon to have the ability to employ many and various types of tools without having to purchase and maintain many complete endoscopic surgical instruments. A replacement tool portion attached to a tool insert having substantially the same configuration can then be installed in the surgical instrument 10.

Articulation control 19 pivots about pivot point 35 and within cut-out portion 62. In the embodiment shown in FIG. 2, the articulation control 19 is movable in a single plane that is indicated by arrow 36. The articulation control 19 according to the present invention can be configured so that its movement in a single plane is matched by the movement of the articulating portion. For example, in the embodiment shown in FIG. 2, up and down movement of the articulation control 19 in a single plane produces movement of the articulating portion in a single plane which substantially corresponds to the movement of the articulation control 19. In other embodiments, such as in the embodiment shown in FIG. 1, side to side movement of the articulation control 19 in a single plane produces substantially corresponding side to side movement of the articulating portion in a single plane. Alternatively, the articulation control can be configured so that side to side movement of the articulation control produces up and down movement of the articulating portion or vice versa. In some instruments, movement of the articulation member does not correspond to the movement of the articulation control. Such design choices are influenced by the nature of the instrument, the preferences of the surgeon, and the like.

FIG. 3 shows, in an isometric view, the opposite side of the handle portion 11 shown in FIG. 2. The second body plate 39 is shown, along with screws 40 which hold the two body plates 39 and 41 together. Protrusions 38 are shown on the articulation control 19 which help prevent the surgeon's thumb from slipping during use of the endoscopic surgical instrument. In some embodiments, cuts in the articulation control 19 are used instead of protrusions for slippage reduction.

Figure 3A:
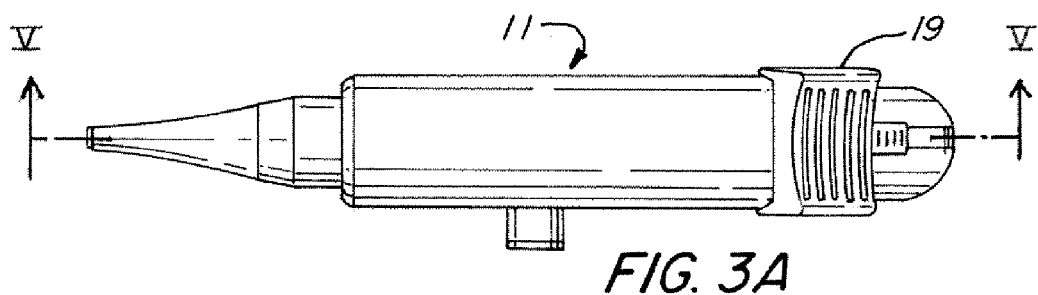
FIG. 3A is a top elevation view of the handle portion of the endoscopic surgical instrument of FIG. 2.

FIG. 3A shows the handle portion 11 of the endoscopic surgical apparatus 10 of FIGS. 2 and 3 in a top elevational view. The articulation control 19 is shown on the proximal end, and the elongated middle portion 12 is shown on the distal end of the handle portion 11. The dotted line V refers to the cross-sectional view of FIG. 5.

FIG. 4 shows the handle portion 11 of FIG. 2 with the plate 39 removed to show the internal parts of the handle portion 11. The articulation control 19 is coupled to the drum 42 at the pivot point 35 (also shown in FIG. 2). Movement of the articulation control 19 rotates the drum 42 accordingly. Drum 42 has anchors 43 which hold the proximal end of control wires 44. The anchors 43 are threaded and adjustable so that the tension of the control wires 44 may be adjusted. The control wires 44 run through the elongated middle portion (not shown in FIG. 4.) to the distal end of the articulating portion (also not shown in FIG. 4). The control wires 44 are partially wrapped around drum 42 and held in place by the anchors 43. The drum 42 shown in FIG. 4 is substantially circular, however, in other embodiments, the drum has an oval, eccentric, or asymmetric shape. The shape of the drum is selected according to the desired degree of articulation control. Wire guides 45 ensure that the control wires exit the handle portion 11 in the proper orientation without interfering with one another or other parts of the endoscopic surgical instrument. The attachment of the drum 42 to the handle portion 11 provides resistance to the movement of articulation control 19. Such resistance reduces unwanted movement of articulation control 19 and thereby serves a "locking" function similar to the locking mechanisms described in relation to the embodiment shown in FIG. 1. In some embodiments, a friction-enhancing coating 84 is applied to the drum 42 and/or the pivot point 35 which helps serve a similar "locking" function.

FIGS. 5 and 5A show in greater detail the control wires 44 and the wire guides 45. The wire guides 45 hold the sheaths 70, which are similar to the coiled wire sheath 32 of the tool insert 30. The control wires 44 run through the sheaths 70 from the wire guides 45 to the distal end of the instrument 10.

Figure 6:
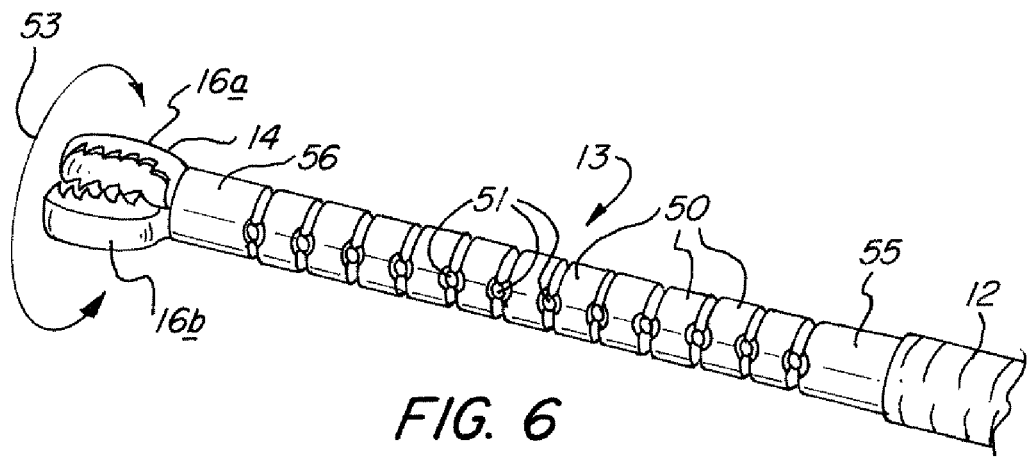
FIG. 6 is an isometric view of the articulating portion of an endoscopic surgical instrument according to an embodiment of the present invention.
Figure 7:
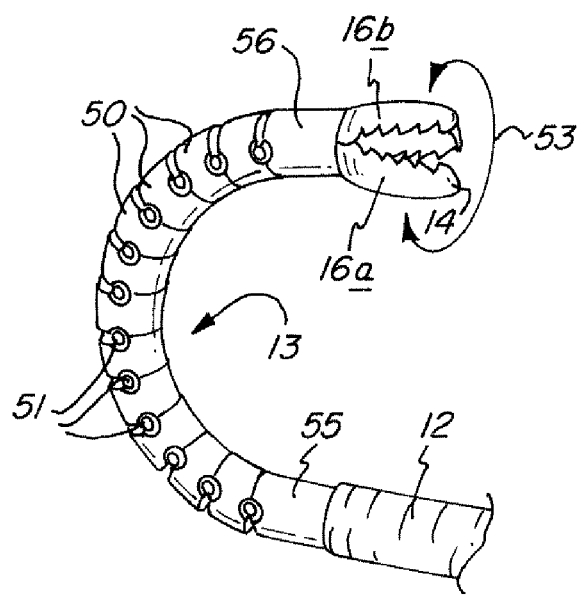
FIG. 7 is an isometric view of the articulating portion of FIG. 6 in a bent position.

FIGS. 6 and 7 show the articulating portion 13 of an endoscopic surgical instrument according to the present invention. The articulating portion 13 is attached by a proximal link member 55 to the distal end of the elongated middle portion 12. The articulating portion is attached to the tool portion 14 by a distal link member 56. The articulating portion 13 is comprised of a series of link members 50 which are connected to each other and to the proximal link member 55 and the distal link member 56 by joint members 51.

Figure 8:
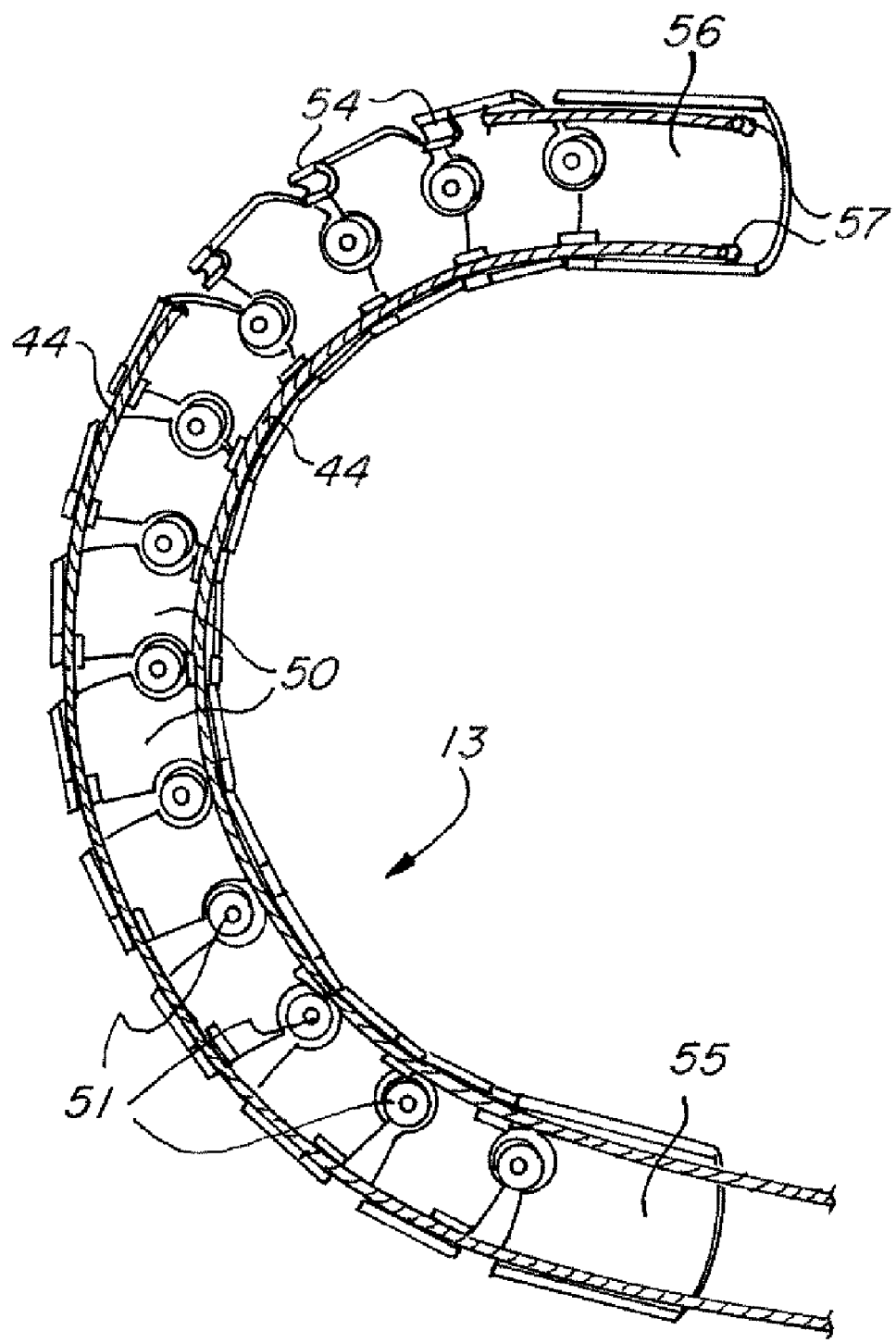
FIG. 8 is a cross-section view of the articulating portion of FIG. 6 in a bent position.

FIG. 7 shows the articulating portion 13 in a bent position. The articulating portion 13 of the embodiment shown in FIGS. 1, 6, 7, and 8 is capable of bending so as to create a 180° curve. The amount of maximum curvature is varied by the design of the shape of the link members 50. FIG. 8 shows the articulating portion 13 bent as in FIG. 7, but in cross-section. The control wires 44 are shown along the sides of the link members 50, disposed within guides 54. The guides 54 do not inhibit axial movement of the control wires 44, but allow them to slide axially in the articulating portion. The guides 54 do, however, retain the control wires 44 against opposite sides of the articulating portion 13. The control wires 44 are attached by lugs at points 57 in the distal link member 56.

Figure 9:
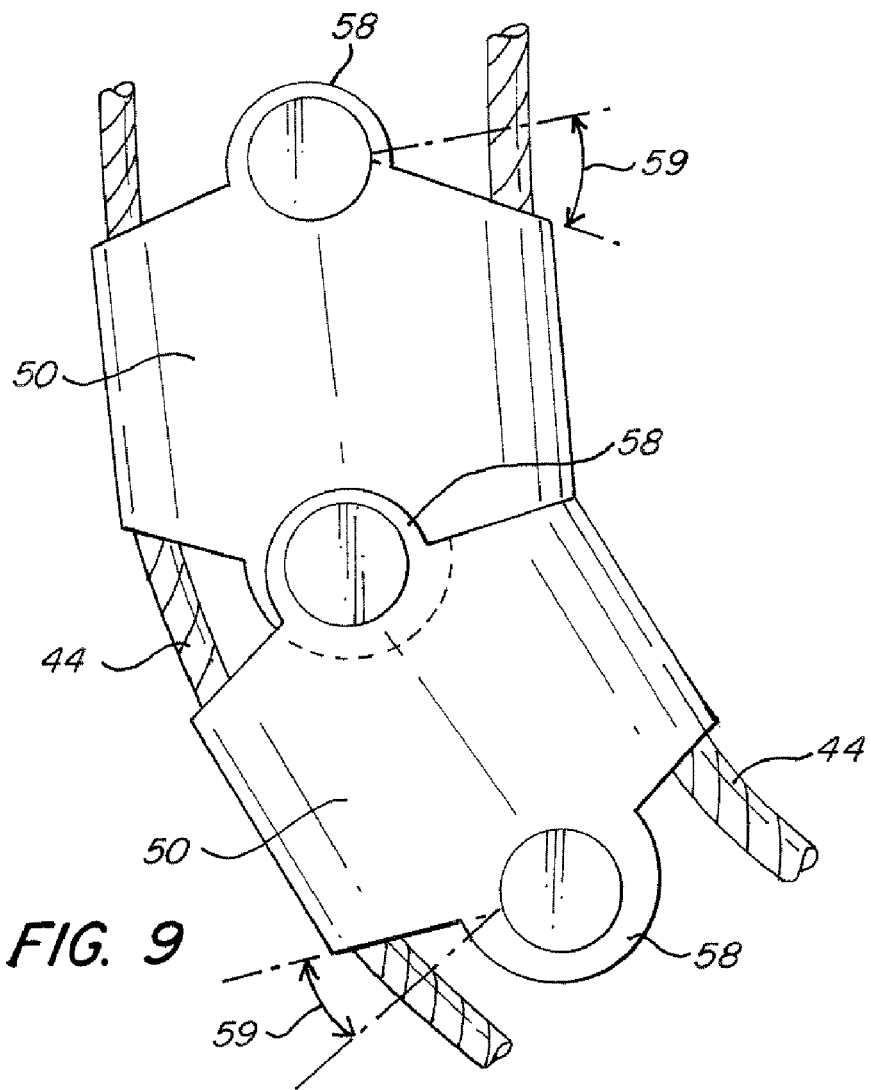
FIG. 9 is an elevation view of two link members of the articulating portion of FIG. 6.

FIG. 9 shows a close up view of two link members 50. The link members 50 are generally cylindrical sections which have been modified. Each link member has a ring 58 on its bottom and top edge for connecting with other link members in a way that permits relative rotation between the link members 50 about the rings 58. As stated above, the amount of permissible bending or articulation in the articulating member 13 is determined by the design of the individual link members 50. The most important aspect of the link member design for this purpose is the size of the angle designated by $\alpha$ in FIG. 9 which determines the size of the cut-out portions 59. The cut-out portions 59 are the parts of a right cylinder that are removed to form the modified cylinder sections of the link members 50. The angle $\alpha$ is the angle between the edge of the theoretical right cylinder and the edge of the modified cylinder. In the embodiment shown in FIGS. 6-9, there are eleven link members and two end link members (proximal link member 55 and distal link member 56), therefore the value of $\alpha$ is 7.5°, since the articulating portion 13 is capable of 180° of articulation. The design of the articulating portion 13 can be adjusted to change not only the total degree of articulation (i.e. 180°, 90°, or 210°), but also the radius of the curvature of the articulating portion. The design is varied by adjusting the size of the link members, the number of link members, and the value of $\alpha$.

The embodiment shown in FIGS. 6-9 shows link members which are substantially hollow. The guides 54 act as openings which align with the lumens in the middle portion 12 designed to receive the control wires. The hollow central portion of the link members accommodates the tool insert 30. In some embodiments, the link members are not substantially hollow, but instead are solid cylindrical sections with portions removed to accommodate the control wires and the tool insert 30.

Articulation of the articulating member 13 is accomplished by increasing the length of one control wire 44 while simultaneously decreasing the length of the other control wire 44 by means of the articulation control 19. When the articulation control 19 on handle portion 11 is moved to one extreme position in its plane of movement, rotation of drum 42 is caused which in turn causes one control wire 44 to be pulled or reeled in the proximal direction. This effectively shortens the control wire 44. At the same time, an equal amount of the other control wire 44 is let out in the distal direction, effectively lengthening it. Because the control wires 44 are anchored at the distal end of the articulating portion 13, the link members 50 will be pulled by the control wire 44 being reeled in. This causes the bending of the articulating portion 13. When the articulation control 19 is moved to its opposite extreme position, the previously shortened control wire 44 is lengthened while the previously lengthened control wire 44 is shortened. This causes the articulating portion 13 to swing in a plane so that the articulating portion 13 is bent 180° on the other side of the axis of the elongated middle portion 12.

FIGS. 6 and 7 also show arrow 53 which indicates the direction of rotation of which the tool portion 14 is capable. When the rotating control 22 shown in FIG. 1 is rotated, this transmits rotational movement via the tool insert 30 to the tool portion 14. The tool portion 14 is rotatable independently of the articulating portion 13, the middle portion 12, and the handle portion 11.

The present invention thus provides very precise control of a surgical tool at a surgical site. The tool portion 14 is easily moved in a plane by the articulating portion 13 and is easily rotated independently of the articulating portion 13. Grabbing, cutting, resecting, pulling, and other surgical tasks are easily and precisely performed. Surgical instruments according to the present invention are also very adaptable to diverse surgical situations as a result of the ease with which the tool inserts are removable and replaceable.

Figure 10:
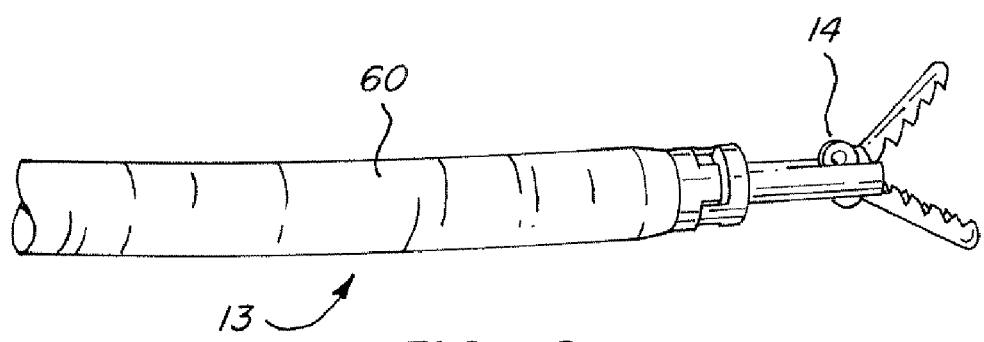
FIG. 10 is an elevation view of an articulating portion and a tool portion of an embodiment of the present invention.

The endoscopic surgical instruments according to the present invention are substantially sealed by conventional methods, particularly the articulating portion and the tool portion, to prevent non-sterile conditions from being created. FIG. 10 shows the articulating portion 13 and tool portion 14 of an embodiment of the present invention wherein the articulating portion is sealed by a flexible cover 60. The flexible cover 60 is formed of a plastic material which is biocompatible. In addition to being substantially sealed, the surgical instruments according to the present invention are capable of sterilization by conventional sterilization methods.

It is also contemplated that the tool inserts which are employed in some embodiments of the present invention are disposable. This feature saves the user of instruments according to the present invention the time and resources associated with cleaning and maintaining the tool inserts.

In some embodiments, the endoscopic surgical instruments according to the present invention are used without the tool portion 14 and the tool insert 30. In such situations, a tubular member is passed into the lumen 66 in the elongated middle portion 12 and out of the distal end of the articulating portion 13 for the delivery or removal of fluid matter to a surgical site. The delivery or removal is highly effective due to the steerable nature of the distal portion of the instrument.

The controls of endoscopic surgical instruments according to the present invention are, in some embodiments, adapted for robotic or electronic control. Such an arrangement makes remote surgery possible, which greatly increases the value of the surgical instruments since they may be employed in a greater number of situations. Robotic or electronic control also provides the maximum amount of precision in the control of the functions of the instrument.

A method of using endoscopic surgical instruments according to the present invention in a transgastric application will now be described. First, a transgastric/transluminal surgical apparatus such as that shown in FIG. 1A is inserted into the patient's stomach. The system enters the patient via the patient's mouth in such a way as to minimize strain and trauma on the patient. In most cases, the surgeon guides the apparatus during insertion with a high degree of accuracy using optical and illumination channels in the apparatus. Once the distal tip of the apparatus reaches the wall of the patient's stomach, an incision is made in the stomach wall by passing a surgical tool through a working channel of the apparatus. Once the incision is complete, the apparatus is pushed through the incision into the peritoneal cavity.

Once the tip of the transgastric/transluminal apparatus reaches the intended surgical site, the surgeon introduces the endoscopic surgical instruments according to the present invention into the apparatus. The surgical instruments are advanced through the apparatus until, as shown in FIG. 1A, the articulating portions 13 are protruding from the channels of the apparatus. The surgeon then performs the surgery using the surgical instruments while viewing the surgical site on a monitor which receives video images via the optical channel of the apparatus. The surgeon may use two surgical instruments according to the present invention, one in each hand, because of the advantageous symmetric design.

Once the surgery is complete, the apparatus is withdrawn from the surgical site back into the stomach. Surgical instruments may again be used to close the incision in the stomach wall by various methods of gastric closure: clips, suture, and the like. Finally, the apparatus is completely withdrawn from the patient's body. The patient's recovery time is relatively short and the risk of infection is relatively low because of the absence of major external incisions and the small size of the incisions that actually were made.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An endoscopic surgical instrument, comprising:
   a handle portion on a proximal end of the endoscopic surgical instrument;
   an elongated middle portion having a length, and comprising a proximal end which is coupled to the handle portion and consisting of components which extend along substantially the entire length of the elongated middle portion that are formed of flexible materials;
   an articulating portion coupled to a distal end of the elongated middle portion comprising a plurality of link members coupled together such that the articulating portion is bendable in a plane;
   a tool portion on a distal end of the endoscopic surgical instrument, coupled to a distal end of the articulating portion; and
   an articulation control member disposed on the handle portion that is moveable in the plane and coupled to the articulating portion to control movement of the articulating portion;
   wherein the plane of movement of the articulation control member substantially corresponds to the plane of movement of the bending of the articulating portion.

2. The endoscopic surgical instrument of claim 1, wherein the elongated middle portion includes at least one lumen along its length and wherein the tool portion is coupled to a tool insert disposed in the elongated middle portion, and the tool insert is coupled at its proximal end to a lever member disposed on the handle portion such that movement of the lever member exerts a force on the tool insert to actuate the tool portion.

3. The endoscopic surgical instrument of claim 2, wherein the tool insert and tool portion are removable as a unit and replaceable with one of a plurality of other tool insert and tool portion units having different configurations.

4. The endoscopic surgical instrument of claim 2, wherein the lever member includes a friction-enhancing coating on a portion thereof to reduce unwanted movement of the lever member.

5. The endoscopic surgical instrument of claim 2, wherein the tool insert is adapted to conduct electricity to the tool portion from a power source which is coupled to the proximal end of the tool insert.

6. The endoscopic surgical instrument of claim 2, wherein the articulation control member and the lever member are simultaneously accessible by a single hand of a user holding the instrument.

7. The endoscopic surgical instrument of claim 6, wherein the articulation control member is positioned to be accessible by a thumb of the single hand holding the endoscopic surgical instrument and the lever member is positioned to be simultaneously accessible by a finger of the single hand holding the endoscopic surgical member.

8. The endoscopic surgical instrument of claim 2, wherein the endoscopic instrument is used for the transmission of fluid matter to or from a surgical site.

9. The endoscopic surgical instrument of claim 2, wherein the handle portion includes a lever lock mechanism which engages a notched portion of the lever member and locks the lever member in a selected position.

10. The endoscopic surgical instrument of claim 9, wherein the endoscopic surgical instrument further comprises two control wires disposed in the elongated middle portion each coupled to the articulation control member and coupled to the distal end of the articulating portion.

11. The endoscopic surgical instrument of claim 10, wherein the control wires and the articulation control member are connected to a drum which is rotatably connected to the handle portion.

12. The endoscopic surgical instrument of claim 10, wherein a drum is rotatably connected to the handle portion, and wherein the control wires and the articulation control member are connected to the drum such that movement of the articulation control member causes rotation of the drum in the plane of movement of the articulation control member, thereby exerting force on the control wires.

13. The endoscopic surgical instrument of claim 10, wherein the handle portion includes a slide lock mechanism which frictionally engages the articulation control member and locks the articulation control member in a selected position.

14. The endoscopic surgical instrument of claim 10, wherein the articulation control member includes a friction-enhancing coating on a portion thereof to reduce unwanted movement of the articulation control member.

15. The endoscopic surgical instrument of claim 10, wherein the tool insert is also coupled to a rotating control member which transmits rotation about the longitudinal axis of the elongated middle portion to the tool insert which in turn rotates the tool portion relative to the articulating portion.

16. The endoscopic surgical instrument of claim 15, wherein the rotating control member rotates in increments among a selected number of fixed positions.

17. The endoscopic surgical instrument of claim 15, wherein the rotating control member includes a friction-enhancing coating on a portion thereof to reduce unwanted movement of the rotating control member.

18. The endoscopic surgical instrument of claim 15, wherein the handle portion includes a rotation lock mechanism which frictionally engages the rotating control member and locks the rotating control member in a selected position.

19. The endoscopic surgical instrument of claim 18, wherein the lever member, the lever lock mechanism, the articulation control member, the slide lock mechanism, the rotating control member, and the rotating lock mechanism are accessible by a single hand of a user of the endoscopic surgical instrument.

20. The endoscopic surgical instrument of claim 18, wherein the lever member, the articulation control member, the rotating control member, and the rotating lock mechanism are simultaneously accessible by a single hand of a user holding the endoscopic surgical instrument.

21. The endoscopic surgical instrument of claim 1, wherein the endoscopic surgical instrument is adapted for use by both a left hand alone and a right hand alone of a user of the endoscopic surgical instrument.

22. The endoscopic surgical instrument of claim 1, wherein the endoscopic surgical instrument is substantially sealed.

23. An endoscopic surgical instrument, comprising:
a handle portion on a proximal end of the endoscopic surgical instrument;
an elongated middle portion having a length, and comprising a proximal end which is coupled to the handle portion, at least one lumen along its length, and consisting of components which extend along substantially the entire length of the elongated middle portion that are formed of flexible materials;
an articulating portion coupled to a distal end of the elongated middle portion comprising a plurality of link members coupled together such that the articulating portion is bendable in a plane;
a tool portion on a distal end of the endoscopic surgical instrument, coupled to a distal end of the articulating portion; and
two control wires each disposed in the elongated middle portion, wherein the two control wires are coupled to an articulation control member disposed on the handle portion and are coupled to the distal end of the articulating portion and wherein the articulation control member is movable in a plane and such movement controls the bending of the articulating portion.

24. The endoscopic surgical instrument of claim 23, wherein the control wires and the articulation control member are connected to a drum which is rotatably connected to the handle portion.

25. The endoscopic surgical instrument of claim 23, wherein a drum is rotatably connected to the handle portion, and wherein the control wires and the articulation control member are connected to the drum such that movement of the articulation control member causes rotation of the drum in the plane of movement of the articulation control member, thereby exerting force on the control wires.

26. The endoscopic surgical instrument of claim 23, wherein the plane of movement of the articulation control member substantially corresponds to the plane of movement of the bending of the articulating portion.

27. The endoscopic surgical instrument of claim 23, wherein the handle portion includes a slide lock mechanism which frictionally engages the articulation control member and locks the articulation control member in a selected position.

28. The endoscopic surgical instrument of claim 23, wherein the articulation control member includes a friction-enhancing coating on a portion thereof to reduce unwanted movement of the articulation control member.

29. The endoscopic surgical instrument of claim 23, wherein the tool portion is coupled to a tool insert disposed in the elongated middle portion, and the tool insert is coupled at its proximal end to a lever member disposed on the handle portion such that movement of the lever member exerts a force on the tool insert to actuate the tool portion.

30. The endoscopic surgical instrument of claim 29, wherein the tool insert and tool portion are removable as a unit and replaceable with one of a plurality of other tool insert and tool portion units having different configurations.

31. The endoscopic surgical instrument of claim 29, wherein the handle portion includes a lever lock mechanism which engages a notched portion of the lever member and locks the lever member in a selected position.

32. The endoscopic surgical instrument of claim 29, wherein the lever member includes a friction-enhancing coating on a portion thereof to reduce unwanted movement of the lever member.

33. The endoscopic surgical instrument of claim 29, wherein the articulation control member and the lever member are disposed on the handle portion so as to be simultaneously accessible by a single hand of a user of the endoscopic surgical instrument.

34. The endoscopic surgical instrument of claim 29, wherein the tool insert is adapted to conduct electricity to the tool portion from a power source which is coupled near the proximal end of the tool insert.

35. The endoscopic surgical instrument of claim 29, wherein the tool insert is also coupled to a rotating control member which transmits rotation about the longitudinal axis of the elongated middle portion to the tool insert which in turn rotates the tool portion relative to the articulating portion.

36. The endoscopic surgical instrument of claim 35, wherein the rotating control member rotates in increments among a selected number of fixed positions.

37. The endoscopic surgical instrument of claim 35, wherein the rotating control member includes a friction-enhancing coating on a portion thereof to reduce unwanted movement of the rotating control member.

38. The endoscopic surgical instrument of claim 35, wherein the handle portion includes a rotation lock mechanism which frictionally engages the rotating control member and locks the rotating control member in a selected position.

39. The endoscopic surgical instrument of claim 23, wherein the endoscopic surgical instrument is adapted for use by both a left hand alone and a right hand alone of a user of the endoscopic surgical instrument.

40. The endoscopic surgical instrument of claim 23, wherein the endoscopic surgical instrument is substantially sealed.

41. The endoscopic surgical instrument of claim 23, wherein the endoscopic instrument is used for the transmission of fluid matter to or from a surgical site.

42. An endoscopic surgical instrument, comprising:
a handle portion on a proximal end of the endoscopic surgical instrument;
an elongated middle portion having a length, and comprising a proximal end which is coupled to the handle portion, at least one lumen along its length, and consisting of components which extend along substantially the entire length of the elongated middle portion that are formed of flexible materials;
an articulating portion coupled to a distal end of the elongated middle portion comprising a plurality of link members coupled together such that the articulating portion is bendable in a plane;

a tool portion on a distal end of the endoscopic surgical instrument, coupled to a distal end of the articulating portion;

two control wires each disposed in the elongated middle portion, wherein the two control wires are coupled to an articulation control member disposed on the handle portion and are coupled to the distal end of the articulating portion and wherein the articulation control member is movable in a plane and such movement controls the bending of the articulating portion; and wherein the plane of movement of the articulation control member substantially corresponds to the plane of movement of the bending of the articulating portion.

43. The endoscopic surgical instrument of claim 42, wherein the tool portion is coupled to a tool insert disposed in the elongated middle portion, and the tool insert is coupled at its proximal end to a lever member disposed on the handle portion such that movement of the lever member exerts a force on the tool insert to actuate the tool portion.

44. The endoscopic surgical instrument of claim 43, wherein the tool insert and tool portion are removable as a unit and replaceable with one of a plurality of other tool insert and tool portion units having different configurations.

45. The endoscopic surgical instrument of claim 43, wherein the articulation control member and the lever member are disposed on the handle portion so as to be simultaneously accessible by a single hand of a user of the endoscopic surgical instrument.

46. The endoscopic surgical instrument of claim 43, wherein the lever member includes a friction-enhancing coating on a portion thereof to reduce unwanted movement of the lever member.

47. The endoscopic surgical instrument of claim 43, wherein the tool insert is also coupled to a rotating control member which transmits rotation about the longitudinal axis of the elongated middle portion to the tool insert which in turn rotates the tool portion relative to the articulating portion.

48. The endoscopic surgical instrument of claim 47, wherein the rotating control member rotates in increments among a selected number of fixed positions.

49. The endoscopic surgical instrument of claim 47, wherein the rotating control member includes a friction-enhancing coating on a portion thereof to reduce unwanted movement of the rotating control member.

50. The endoscopic surgical instrument of claim 47, wherein the handle portion includes a slide lock mechanism which frictionally engages the articulation control member and locks the articulation control member in a selected position.

51. The endoscopic surgical instrument of claim 50, wherein the handle portion includes a lever lock mechanism which engages a notched portion of the lever member and locks the lever member in a selected position.

52. The endoscopic surgical instrument of claim 51, wherein the handle portion includes a rotation lock mechanism which frictionally engages the rotating control member and locks the rotating control member in a selected position.

53. The endoscopic surgical instrument of claim 52, wherein the lever member, the lever lock mechanism, the articulation control member, the slide lock mechanism, the rotating control member, and the rotating lock mechanism are accessible by a single hand of a user of the endoscopic surgical instrument.

54. The endoscopic surgical instrument of claim 42, wherein the control wires and the articulation control member are connected to a drum which is rotatably connected to the handle portion.

55. The endoscopic surgical instrument of claim 42, wherein a drum is rotatably connected to the handle portion, and wherein the control wires and the articulation control member are connected to the drum such that movement of the articulation control member causes rotation of the drum in the plane of movement of the articulation control member, thereby exerting force on the control wires.

56. The endoscopic surgical instrument of claim 42, wherein the plane of movement of the articulation control member substantially corresponds to the plane of movement of the bending of the articulating portion.

57. The endoscopic surgical instrument of claim 42, wherein the articulation control member includes a friction-enhancing coating on a portion thereof to reduce unwanted movement of the articulation control member.

58. The endoscopic surgical instrument of claim 42, wherein the endoscopic surgical instrument is adapted for use by both a left hand alone and a right hand alone of a user of the endoscopic surgical instrument.

59. The endoscopic surgical instrument of claim 42, wherein the endoscopic surgical instrument is substantially sealed.

60. The endoscopic surgical instrument of claim 42, wherein the endoscopic surgical instrument is used for the transmission of fluid matter to or from a surgical site.

61. An endoscopic surgical instrument, comprising:
a handle portion on a proximal end of the endoscopic surgical instrument;
an elongated middle portion having a length, and comprising a proximal end which is coupled to the handle portion and consisting of components which extend along substantially the entire length of the elongated middle portion that are formed of flexible materials;
an articulating portion coupled to a distal end of the elongated middle portion comprising a plurality of link members coupled together such that the articulating portion is bendable in a plane; and
a tool portion on a distal end of the endoscopic surgical instrument, coupled to a distal end of the articulating portion;
wherein the elongated middle portion includes at least one lumen along its length and wherein the tool portion is coupled to a tool insert disposed in the elongated middle portion, and the tool insert is coupled at its proximal end to a lever member disposed on the handle portion such that movement of the lever member exerts a force on the tool insert to actuate the tool portion; and
wherein the tool insert is also coupled to a rotating control member which transmits rotation about the longitudinal axis of the elongated middle portion to the tool insert which in turn rotates the tool portion relative to the articulating portion.

62. The endoscopic surgical instrument of claim 61, wherein the rotating control member rotates in increments among a selected number of fixed positions.

63. The endoscopic surgical instrument of claim 61, wherein the rotating control member includes a friction-enhancing coating on a portion thereof to reduce unwanted movement of the rotating control member.

64. The endoscopic surgical instrument of claim 61, wherein the handle portion includes a rotation lock mechanism which frictionally engages the rotating control member and locks the rotating control member in a selected position.

65. The endoscopic surgical instrument of claim 64, further comprising an articulation control member disposed on the handle portion that is moveable in the plane and coupled to the articulating portion to control movement of the articulating portion wherein the plane of movement of the articulation control member substantially corresponds to the plane of movement of the bending of the articulating portion.

* * * * *